(12) United States Patent
Smith et al.

(10) Patent No.: US 8,980,622 B2
(45) Date of Patent: Mar. 17, 2015

(54) BIOLOGICAL STERILIZATION INDICATOR AND METHOD OF USING SAME

(75) Inventors: Jeffrey D. Smith, Marine on St. Croix, MN (US); Jeffrey C. Pederson, Minneapolis, MN (US); Sailaja Chandrapati, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 433 days.

(21) Appl. No.: 13/384,886

(22) PCT Filed: Jul. 6, 2010

(86) PCT No.: PCT/US2010/041010
§ 371 (c)(1),
(2), (4) Date: Jan. 19, 2012

(87) PCT Pub. No.: WO2011/011189
PCT Pub. Date: Jan. 27, 2011

(65) Prior Publication Data
US 2012/0149094 A1 Jun. 14, 2012

Related U.S. Application Data

(60) Provisional application No. 61/226,937, filed on Jul. 20, 2009.

(51) Int. Cl.
*C12M 1/34* (2006.01)
*A61L 2/28* (2006.01)
*C12Q 1/22* (2006.01)

(52) U.S. Cl.
CPC .... *A61L 2/28* (2013.01); *C12Q 1/22* (2013.01)
USPC ................. 435/287.4; 435/283.1; 435/287.1; 435/287.6; 435/288.1

(58) Field of Classification Search
CPC ........... G01N 31/226; C12Q 1/22; A61L 2/28
USPC ........... 435/283.1, 287.1, 287.4, 287.6, 288.1
See application file for complete search history.

(56) References Cited

U.S. PATENT DOCUMENTS 3,440,144 A 4/1969 Andersen
3,661,717 A 5/1972 Nelson
(Continued)

FOREIGN PATENT DOCUMENTS

EP 0078112 5/1983
EP 0152298 8/1985
(Continued)

OTHER PUBLICATIONS

International Search Report PCT/US2010/041010 Nov. 26, 2010, 5 pgs.
(Continued)

*Primary Examiner* — Nathan Bowers
(74) *Attorney, Agent, or Firm* — Nicole J. Einerson

(57) ABSTRACT

A biological sterilization indicator (BI) and a method of using same for assaying the lethality of a sterilization process. The BI can include a housing, which can include a first portion, and a second portion, which can be movable with respect to the first portion between a first and second position. The BI can further include a frangible container comprising a liquid. The BI can further include a spore reservoir and a projection positioned in the housing. The projection can be configured to fracture the container when the second portion of the housing is moved from the first position to the second position. The method can include maintaining a minimal cross-sectional area of space around the container when the second portion of the housing is in the first position, and fracturing the container in response to moving the second portion between the first and second positions.

20 Claims, 9 Drawing Sheets

(56) References Cited

U.S. PATENT DOCUMENTS

| | | |
|---|---|---|
| 3,907,106 A | 9/1975 | Purrmann |
| 4,291,122 A | 9/1981 | Orelski |
| 4,304,869 A | 12/1981 | Dyke |
| 4,461,837 A | 7/1984 | Karle |
| 4,528,268 A | 7/1985 | Andersen |
| 4,596,773 A | 6/1986 | Wheeler, Jr. |
| 4,717,661 A | 1/1988 | McCormick |
| 4,732,850 A | 3/1988 | Brown |
| 4,743,537 A | 5/1988 | McCormick |
| 4,883,641 A | 11/1989 | Wicks |
| 4,885,253 A | 12/1989 | Kralovic |
| 5,073,488 A | 12/1991 | Matner |
| 5,167,923 A | 12/1992 | Van Iperen |
| 5,223,401 A | 6/1993 | Foltz |
| 5,252,484 A | 10/1993 | Matner |
| 5,405,580 A | 4/1995 | Palmer |
| 5,418,167 A | 5/1995 | Matner |
| 5,482,171 A | 1/1996 | Palmer |
| 5,500,184 A * | 3/1996 | Palmer .................. 422/2 |
| 5,552,320 A | 9/1996 | Smith |
| 5,736,355 A | 4/1998 | Dyke |
| 5,750,184 A | 5/1998 | Imburgia |
| 5,770,393 A | 6/1998 | Dalmasso |
| 5,801,010 A | 9/1998 | Falkowski |
| 5,866,356 A | 2/1999 | Albert |
| 5,872,004 A | 2/1999 | Bolsen |
| 5,955,296 A | 9/1999 | Roll |
| 6,025,189 A | 2/2000 | Bolea |
| 6,352,837 B1 | 3/2002 | Witcher |
| 6,623,955 B2 | 9/2003 | Matner |
| 6,904,370 B1 | 6/2005 | Levinson |
| 6,924,139 B2 | 8/2005 | Eveland |
| 7,223,364 B1 | 5/2007 | Johnston |
| 8,541,196 B2 * | 9/2013 | Sestak et al. .................. 435/31 |
| 2003/0133830 A1 | 7/2003 | Gonzalez |
| 2003/0186458 A1 * | 10/2003 | DiCesare et al. ............. 436/172 |
| 2003/0235677 A1 | 12/2003 | Hanschen |
| 2004/0197848 A1 | 10/2004 | Behun |
| 2005/0014214 A1 | 1/2005 | Eveland |
| 2005/0074833 A1 | 4/2005 | Gillis |
| 2006/0263258 A1 | 11/2006 | Harris |
| 2008/0070231 A1 | 3/2008 | Franciskovich |
| 2008/0070272 A1 | 3/2008 | Franciskovich |
| 2008/0206801 A1 | 8/2008 | Dallmier |
| 2008/0261296 A1 | 10/2008 | Justi |
| 2008/0297864 A1 | 12/2008 | Horgan |

FOREIGN PATENT DOCUMENTS

| | | |
|---|---|---|
| WO | WO 01/13964 | 3/2001 |
| WO | WO 04/000569 | 12/2003 |
| WO | WO 2007/070310 | 6/2007 |
| WO | WO 2010/045138 | 4/2010 |

OTHER PUBLICATIONS

3M™ Attest™ 1292-S Biological Indicator for Steam 3M™ Attest™ Auto-Readers, (2007), pp. 1-14.

The State Intellectual Property Office of The People's Republic of China Search Report; CN App No. 201080040700.3; May 6, 2013; 3 pgs.

* cited by examiner

BIOLOGICAL STERILIZATION INDICATOR AND METHOD OF USING SAME

CROSS REFERENCE TO RELATED APPLICATIONS

This is a national stage filing under 35 U.S.C. §371 of PCT/US2010/041010, filed Jul. 6, 2010, which claims priority to U.S. Provisional Application No. 61/226,937, filed Jul. 20, 2009, the disclosure of which is incorporated herein by reference in its entirety.

FIELD

The present disclosure generally relates to sterilization indicators, and particularly, to biological sterilization indicators.

BACKGROUND

In a variety of industries, such as the health care industry but also in other industrial applications, it can be necessary to monitor the effectiveness of processes used to sterilize equipment such as medical devices, instruments and other disposable and non-disposable articles. In these settings, sterilization is generally defined as the process of completely destroying all viable microorganisms including structures such as viruses and spores. As a standard practice, hospitals include a sterility indicator with a batch of articles to assay the lethality of the sterilization process. Both biological and chemical sterility indicators have been used.

One standard type of biological sterility indicator includes a known quantity of test microorganisms, for example *Geobacillus stearothermophilus* (formerly *Bacillus stearothermophilus*) or *Bacillus atrophaeus* (formerly *Bacillus subtilis*) spores, which are many times more resistant to a sterilization process than most contaminating organisms. After the indicator is exposed to the sterilization process, the spores can be incubated in a nutrient medium to determine whether any of the spores survived the sterilization process, with spore growth indicating that the sterilization process was insufficient to destroy all of the microorganisms. Although advances have been made, the time period for determining this with certainty can be undesirably long.

Available chemical sterility indicators can be read immediately at the end of the sterilization process. However, the results indicate only that a particular condition was present during the sterilization process, such as the presence of a particular chemical or a temperature, and potentially, that the condition was reached for a certain period of time.

It is generally considered that the response of living organisms to all conditions actually present is a more direct and reliable test for how effective a sterilization process is in achieving sterilization. Accordingly, there is a continuing need for biological sterility indicators, which can indicate the effectiveness of a sterilization process without an excessive delay after completion of the sterilization process, and yet can provide a high level of confidence that various sterility parameters were reached in the sterilization process.

SUMMARY

One aspect of the present disclosure provide a biological sterilization indicator. The biological sterilization indicator can include a housing, which can include a first portion, and a second portion adapted to be coupled to the first portion. The second portion can be movable with respect to the first portion between a first position and a second position. The biological sterilization indicator can further include a container comprising a liquid. At least a portion of the container can be frangible, and the container can be positioned in at least the first portion of the housing. The biological sterilization indicator can further include a spore reservoir positioned in the housing, and a projection positioned in the housing. The projection can be configured to (a) hold the container intact in a location in the housing in which a minimal cross-sectional area of space between the container and at least one of the housing and the projection is maintained when the second portion of the housing is in the first position, and (b) fracture the container when the second portion of the housing is moved from the first position to the second position.

Another aspect of the present disclosure provides a biological sterilization indicator. The biological sterilization indicator can include a housing, which can include a first portion, and a second portion adapted to be coupled to the first portion. The second portion can be movable with respect to the first portion between a first position and a second position. The biological sterilization indicator can further include a container comprising a liquid. At least a portion of the container can be frangible, and the container can be positioned in at least the first portion of the housing. The biological sterilization indicator can further include a spore reservoir positioned in the housing, a carrier positioned to hold the container intact in a location in the housing when the second portion of the housing is in the first position, and a projection positioned to fracture the container when the second portion of the housing is moved from the first position to the second position. The carrier can be positioned to allow the container to move in response to movement of the second portion of the housing between its first position and the second position. In addition, the carrier can be positioned to maintain at least a minimal cross-sectional area of space defined between the container and at least one of the housing, the carrier, and the projection.

Another aspect of the present disclosure provides a method for assaying the lethality of a sterilization process. The method can include providing a biological sterilization indicator including a housing, which can include a first portion, and a second portion adapted to be coupled to the first portion. The second portion of the housing can be movable with respect to the first portion between a first position and a second position. The method can further include providing a container comprising a liquid. At least a portion of the container can be frangible, and the container can be positioned in at least the first portion of the housing. The method can further include providing a spore reservoir positioned in the housing. The method can further include maintaining a minimal cross-sectional area of space around the container when the second portion of the housing is in the first position. The method can further include moving the second portion of the housing with respect to the first portion of the housing from the first position to the second position, and fracturing the container in response to moving the second portion from the first position to the second position.

Other features and aspects of the present disclosure will become apparent by consideration of the detailed description and accompanying drawings.

DETAILED DESCRIPTION

Figure 1:
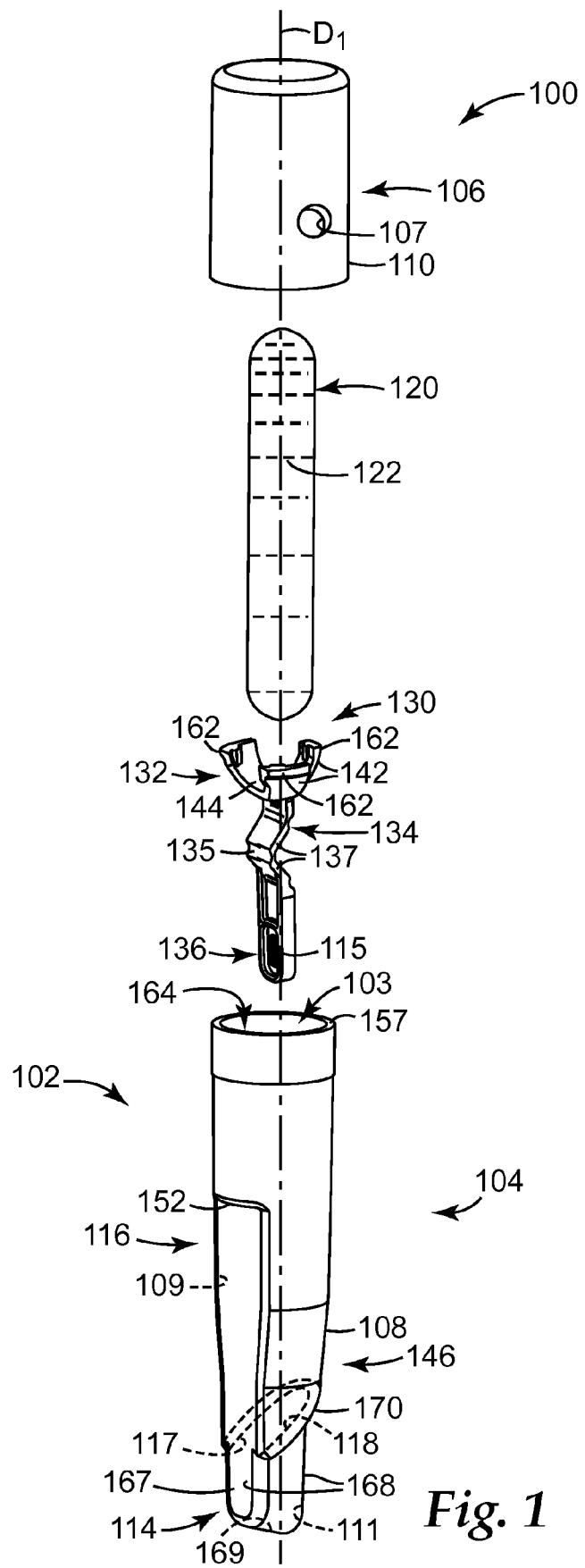
FIG. 1 is a perspective exploded view of a biological sterilization indicator according to one embodiment of the present disclosure, the biological sterilization indicator including an insert.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "supported," and "coupled" and variations thereof are used broadly and encompass both direct and indirect supports and couplings. Further, "connected" and "coupled" are not restricted to physical or mechanical connections or couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to a sterilization indicator, and particularly, to a biological sterilization indicator. A biological sterilization indicator is also sometimes referred to as a "biological sterility indicator," or simply, a "biological indicator." Some embodiments of the biological sterilization indicator of the present disclosure are self-contained, and can be used to determine the lethality of a sterilizing process. The present disclosure generally relates to the construction of the biological sterilization indicator that allows for one or more of at least the following: housing a liquid separate from spores during sterilization and allowing for combination of the liquid and spores after sterilization; holding a frangible container (e.g., an ampoule) that contains the liquid (e.g., in a location separate from spores in the biological sterilization indicator during sterilization); releasing the liquid from the frangible container (e.g., during activation of the biological sterilization indicator) and/or controlling the movement of the liquid to a spore location in the biological sterilization indicator; allowing for movement of the container in the biological sterilization indicator; providing a substantially constant sterilant path; collecting and/or retaining portions of the fractured container (e.g., to inhibit movement of the fractured portions to the proximity of the spores); and/or minimizing diffusion of spores and/or signals away from a spore location or a detection region of the biological sterilization indicator (e.g., to enhance detection).

Generally, microorganisms are chosen to be used in a biological sterilization indicator that are resistant to a particular sterilization process. The biological sterilization indicators of the present disclosure include a viable culture of a known species of microorganism, usually in the form of microbial spores. The test microorganism in the biological sterilization indicator is either killed by a successful sterilization cycle, or survives if the sterilization cycle is not adequate for some reason. Bacterial spores, rather than the vegetative form of the organisms, are sometimes used at least partly because vegetative bacteria are known to be relatively easily killed by sterilizing processes. Spores also have superior storage characteristics and can remain in their dormant state for years. As a result, sterilization of an inoculum of a standardized spore strain provides a high degree of confidence that inactivation of all microorganisms in a sterilizing chamber has occurred.

By way of example only, the present disclosure describes the microorganisms used in the biological sterilization indicator as being "spores;" however, it should be understood that the type of microorganism (e.g., spore) used in a particular embodiment of the biological sterilization indicator is selected for being highly resistant to the particular sterilization process contemplated. Accordingly, different embodiments of the present disclosure may use different microorganisms, depending on the sterilization process for which the particular embodiment is intended. The term "spores" is used throughout the present disclosure for simplicity, but it should be understood that other forms of microorganisms, enzymes, or a combination thereof, can be used in the biological sterilization indicator of the present disclosure instead.

The biological sterilization indicator of the present disclosure can be used with a variety of sterilization processes including, but not limited to, exposure to steam (e.g., pressurized steam), dry heat, gaseous or liquid agents (e.g., ethylene oxide, hydrogen peroxide, peracetic acid, ozone, or combinations thereof), radiation, or combinations thereof. In at least some of the sterilization processes, an elevated temperature, for example, 50° C., 100° C., 121° C., 132° C., 134° C., or the like, is included or may be encountered in the process. In addition, elevated pressures and/or a vacuum may be encountered, for example, 15 psi ($1 \times 10^5$ Pa)

The spores used in a particular system are selected according to the sterilization process used. For example, for a steam sterilization process, *Geobacillus stearothermophilus* or *Bacillus stearothermophilus* can be used. In another example, for an ethylene oxide sterilization process, *Bacillus atrophaeus* (formerly *Bacillus subtilis*) can be used. In some embodiments, the sterilization process resistant spores can include, but are not limited to, at least one of *Geobacillus stearothermophilus, Bacillus stearothermophilus, Bacillus subtilis, Bacillus atrophaeus, Bacillus megaterium, Bacillus coagulans, Clostridium sporogenes, Bacillus pumilus*, or combinations thereof.

Enzymes and substrates that can be suitable for use in the biological sterilization indicator of the present disclosure are identified in U.S. Pat. Nos. 5,073,488 (Matner et al), 5,418,167 (Matner et al.), and 5,223,401 (Foltz et al.), which are incorporated herein by reference for all they disclose.

Suitable enzymes can include hydrolytic enzymes and/or enzymes derived from spore-forming microorganisms, such as Bacillus stearothermophilus and *Bacillus subtilis*. Enzymes from spore-forming microorganisms that can be useful in the biological sterilization indicators of the present disclosure can include beta-D-glucosidase, alpha-D-glucosidase, alkaline phosphatase, acid phosphatase, butyrate esterase, caprylate esterase lipase, myristate lipase, leucine aminopeptidase, valine aminopeptidase, chymotrypsin, phosphohydrolase, alpha-D-galactosidase, beta-D-galactosidase, tyrosine aminopeptidase, phenylalanine aminopeptidase, beta-D-glucuronidase, alpha-L-arabinofuranosidase, N-acetyl-beta-glucosaminodase, beta-D-cellobiosidase, alanine aminopeptidase, proline aminopeptidase and fatty acid esterases.

Chromogenic and fluorogenic substrates that react with enzymes to form detectable products, and that are suitable for use in the sterilization indicator of the present disclosure, are well known in the art. (M. Roth, *Methods of Biochemical Analysis*, Vol. 17, D. Block, Ed., Interscience Publishers, New York, 1969, p. 89, incorporated herein by reference; S. Udenfriend, *Fluorescence Assay in Biology and Medicine*, Academic Press, New York, 1962, p. 312; and D. J. R. Lawrence, *Fluorescence Techniques for the Enzymologist*, Methods in Enzymology, Vol. 4, S. P. Colowick and N. O. Kaplan, Eds., Academic Press, New York, 1957, p. 174). These substrates may be classified in two groups based on the manner in which they create a visually detectable signal. The substrates in the first group react with enzymes to form enzyme-modified products that are themselves chromogenic or fluorescent. The substrates in the second group form enzyme-modified products that must react further with an additional compound, or compounds, to generate a color or fluorescent signal.

In some embodiments, the source of active enzyme can be (1) the purified, isolated enzyme derived from an appropriate microorganism; (2) a microorganism to which the enzyme is indigenous or added by genetic engineering; and/or (3) a microorganism to which the enzyme has been added during sporulation or growth, such that the enzyme is incorporated or associated with the microorganism, e.g., an enzyme added to a spore during sporulation which becomes incorporated within the spore. In some embodiments, the microorganisms which may be utilized as the source of an enzyme include bacteria or fungi in either the spore or vegetative state. In some embodiments, the enzyme source includes *Bacillus, Clostridium, Neurospora, Candida*, or a combination of such species of microorganisms.

The enzyme alpha-D-glucosidase has been identified in spores of *Bacillus stearothermophilus*, such as those commercially available as "ATCC 8005" and "ATCC 7953" from American Type Culture Collection, Rockville, Md. The enzyme beta-D-glucosidase has been found in *B. subtilis* (e.g., commercially available as "ATCC 9372" from American Type Culture Collection).

In the event that an isolated enzyme is utilized, or the microorganism used as the source of the enzyme is not more resistant to the sterilization conditions than the natural contaminants, another microorganism commonly used to monitor sterilization conditions can be exposed to the sterilization cycle along with the enzyme source. In such a case, the method of the present disclosure may include the step of incubating any viable microorganism remaining after the sterilization cycle with an aqueous nutrient medium to confirm the sterilization efficacy.

In general, monitoring the effectiveness of the sterilization process can include placing the biological sterilization indicator of the present disclosure in a sterilizer. In some embodiments, the sterilizer includes a sterilization chamber that can be sized to accommodate a plurality of articles to be sterilized, and can be equipped with a means of evacuating air and/or other gases from the chamber and a means for adding a sterilant to the chamber. The biological sterilization indicator of the present disclosure can be positioned in areas of the sterilizer that are most difficult to sterilize (e.g., above the drain). Alternately, the biological sterilization indicator of the present disclosure can be positioned adjacent (or in the general proximity of) an article to be sterilized when the biological sterilization indicator is positioned in the sterilization chamber. In addition, the biological sterilization indicator can be positioned in process challenge devices that can be used in sterilizers.

The sterilization process can further include exposing the article(s) to be sterilized and the biological sterilization indicator to a sterilant. In some embodiments, the sterilant can be added to the sterilization chamber after evacuating the chamber of at least a portion of any air or other gas present in the chamber. Alternatively, sterilant can be added to the chamber without evacuating the chamber. A series of evacuation steps can be used to assure that the sterilant reaches all desired areas within the chamber and contacts all desired article(s) to be sterilized, including the biological sterilization indicator.

In general, after the biological sterilization indicator has been exposed to a sterilization cycle, a liquid (e.g., a growth media, water that can be mixed with a solid growth media, etc., or combinations thereof) can be introduced to the spores. The step in which the liquid is introduced to the spores can be referred to the "activation step." If the spores have survived the sterilization cycle, the liquid will facilitate growth of the spores, and such growth can be investigated. If growth is observed, the sterilization cycle is generally deemed ineffective.

Some existing systems include a glass ampoule inside the biological indicator that can be broken by squeezing or bending the biological indicator (e.g., by hand), or by compression of a cap against an ampoule, forcing the ampoule to fracture with the cap. Such existing systems, however, can have various limitations or potential hazards associated with them.

Fracturing the ampoule by bending or squeezing the biological indicator can potentially cause personal injury, for example, if the broken glass cuts through a wall of the biological indicator. This can be particularly problematic if the biological indicator is still warm from a sterilization cycle that has softened the walls of the biological indicator. Bending the biological indicator can also create opaque creases caused by over-stressing the biological indicator wall (e.g., if the wall is formed of plastic), which can interfere with detection of spore growth (e.g., if optical methods are used to elucidate spore growth).

In addition, in existing systems that employ cap-actuated ampoule breakage, ampoule breakage can be accomplished by forcing the ampoule into a constriction, causing it to fracture. The amount of force required to fracture the ampoule with such methods can be quite high, which can create an ergonomic problem for the user. Some existing systems that use cap activation include wedges or shims attached to the cap that lodge against the side of the ampoule to fracture it. In such systems, the ampoule is often broken near the top of the ampoule (e.g., adjacent a midpoint of the ampoule or higher), which can leave the lower section of the ampoule intact, which can allow liquid from the ampoule to be retained in the bottom of the ampoule, and which can reduce the amount of liquid that is available to the spores. In addition, in some existing systems, portions of the ampoule or frangible container (e.g., glass shards) can accumulate near the spores, which can reduce the availability of the liquid to the spores, and which can interfere with detection of spore growth.

Some embodiments of the present disclosure, on the other hand, provide optimal and safe breakage of a frangible container with relatively low force, while enhancing transfer of liquid to the spore region of the biological sterilization indicator, and/or enhancing containment of the liquid in the spore region of the biological sterilization indicator. In addition, some embodiments of the present disclosure operate to drive a liquid to a particular area of the biological sterilization indicator, such as a spore detection area of the biological sterilization indicator.

FIGS. 1-5 illustrate a biological sterilization indicator 100 according to one embodiment of the present disclosure. The biological sterilization indicator 100 can include a housing 102, which can include a first portion 104 and a second portion 106 (e.g., a cap) adapted to be coupled together to provide a self-contained biological sterilization indicator. In some embodiments, the first portion 104 and second portion 106 can be formed of the same materials, and in some embodiments, the first portion 104 and the second portion 106 can be formed of different materials.

Figure 4:
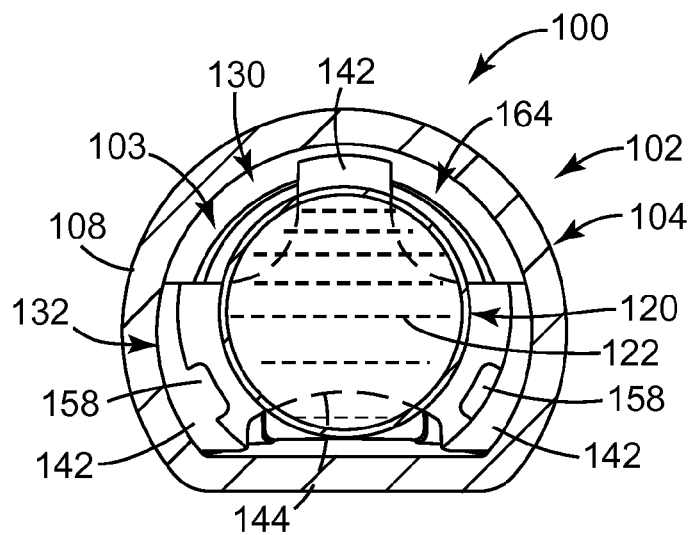
FIG. 4 is a top cross-sectional view of the biological sterilization indicator of FIGS. 1-3, before activation.

The housing 102 can be defined by at least one liquid impermeable wall, such as a wall 108 of the first portion 104 and/or a wall 110 of the second portion 106. It should be understood that a one-part unitary housing 102 may also be employed or that the first and second portions 104 and 106 can take on other shapes dimensions and relative structures without departing from the spirit and scope of the present disclosure. Suitable materials for the housing 102 (e.g., the walls 108 and 110) can include, but are not limited to, a glass, a metal (e.g., foil), a polymer (e.g., polycarbonate, polypropylene, polythyene, polystyrene, polyester, polymethyl methacrylate (PMMA or acrylic), acrylonitrile butadiene styrene (ABS), cyclo olefin polymer (COP), cyclo olefin copolymer (COC), polysulfone (PSU), polyethersulfone (PES), polyetherimide (PEI), polybutyleneterephthalate (PBT)), a ceramic, a porcelain, or combinations thereof In some embodiments, the biological sterilization indicator 100 can further include a frangible container 120 that contains a liquid 122. The frangible container 120 can be formed of a variety of materials, including, but not limited to, one or more of metal (e.g., foil), a polymer (e.g., any of the polymers listed above with respect to the housing 102), glass (e.g., a glass ampoule), and combinations thereof. In some embodiments, only a portion of the container 120 is frangible, for example, the container 120 can include a frangible cover (e.g., a frangible barrier, film, membrane, or the like). FIG. 4 shows a top cross-sectional view of the biological sterilization indicator 100 taken at a location near the bottom of the container 120.

Figure 2:
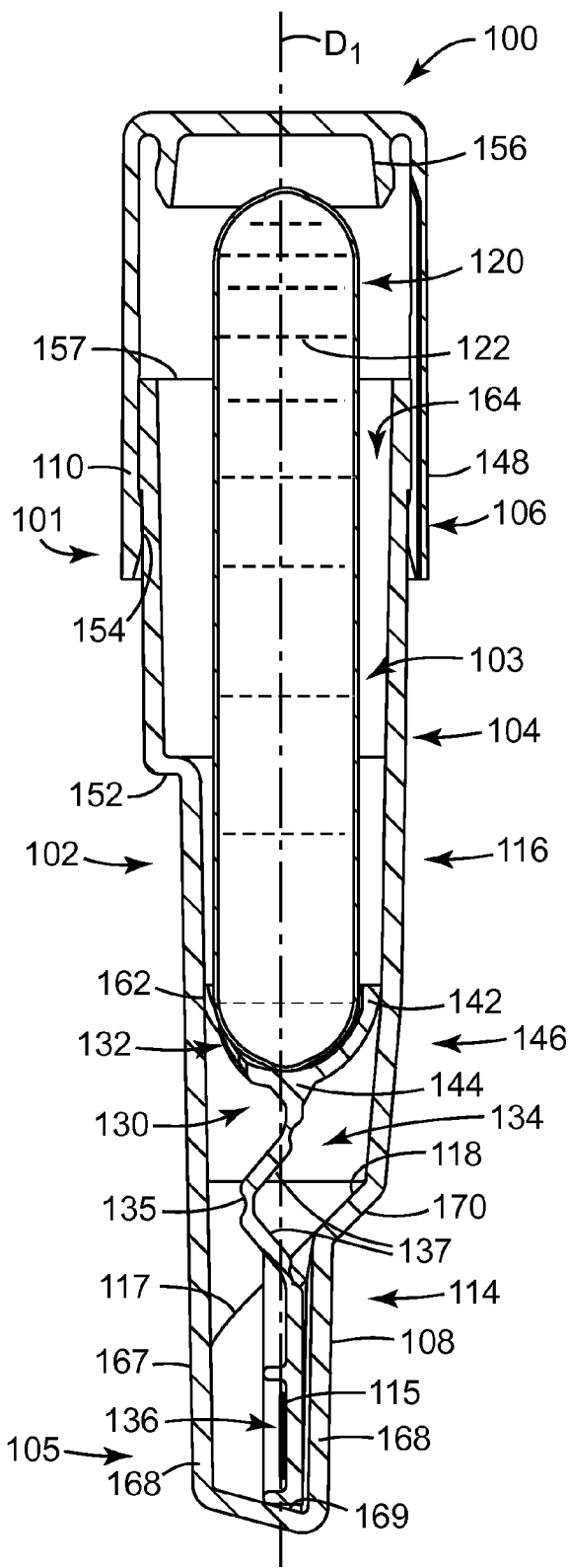
FIG. 2 is an assembled side cross-sectional view of the biological sterilization indicator of FIG. 1, before activation.

The first portion 104 of the housing 102 can be adapted to house a majority of the components of the biological sterilization indicator 100. The housing 102 can include a reservoir 103 that can be defined by one or both of the first portion 104 and the second portion 106 of the housing 102. The biological sterilization indicator 100 can further include spores 115 or a locus of spores positioned in fluid communication with the reservoir 103. As shown in FIG. 1, the second portion 106 of the housing 102 can include one or more apertures 107 to provide fluid communication between the interior of the housing 102 (e.g., the reservoir 103) and ambience. For example, the one or more apertures 107 can provide fluid communication between the spores 115 and ambience during a sterilization process, and can serve as an inlet into the biological sterilization indicator 100 and as an inlet of a sterilant path 164 (described in greater detail below). In some embodiments, as shown in FIG. 2, the second portion 106 of the housing 102 can be coupled to a first end 101 of the first portion 104 of the housing 102, and the spores 115 can be positioned at a second end 105, opposite the first end 101, of the first portion 104 of the housing 102.

In some embodiments, a barrier (e.g., a sterile barrier; not shown) can be positioned in the sterilant path 164 (e.g., at the inlet formed by the aperture 107) to inhibit contaminating or foreign organisms, objects or materials from entering the biological sterilization indicator 100. Such a barrier can include a gas-transmissive, microorganism-impermeable material, and can be coupled to the housing 102 by a variety of coupling means, including, but not limited to, an adhesive, a heat seal, sonic welding, or the like. Alternatively, the barrier can be coupled to the sterilant path 164 via a support structure (such as the second portion 106) that is coupled to the first portion 104 of the housing 102 (e.g.,. in a snap-fit engagement, a screw-fit engagement, a press-fit engagement, or a combination thereof). During exposure to a sterilant, the sterilant can pass through the barrier into the sterilant path 164 and into contact with the spores 115.

In some embodiments, as shown in FIGS. 1-5, the housing 102 can include a lower portion 114 and an upper portion 116, which can be at least partially separated by an inner wall 118, ledge, partition, or the like, in which can be formed an opening 117 that provides fluid communication between the lower portion 114 and the upper portion 116. In some embodiments, as shown in FIGS. 1-5, the lower portion 114 of the first portion 104 of the housing 102 (sometimes referred to as "the lower portion 114" or the "the lower portion 114 of the housing 102" for simplicity, or as the "spore growth chamber") can be adapted to house the spores 115 or a locus of spores. In some embodiments, the lower portion 114 can be referred to as the "detection portion" or "detection region" of the housing 102, because at least a portion of the lower portion 114 can be interrogated for signs of spore growth. In addition, in some embodiments, the upper portion 116 of the first portion 104 of the housing 102 (sometimes referred to as "the upper portion 116" or the "the upper portion 116 of the housing 102" for simplicity) can be adapted to house at least a portion of the frangible container 120, particularly, before activation.

In some embodiments, the wall 118 (sometimes referred to as a "separating wall") can be angled or slanted, for example, oriented at a non-zero and non-right angle with respect to a longitudinal direction $D_1$ of the housing 102 (e.g., where the longitudinal direction $D_1$ extends along the length of the housing 102). Such angling or slanting of the wall 118 can facilitate the movement of the liquid 122 from the upper portion 116 to the lower portion 114 after sterilization and after the container 120 has been broken to release the liquid 122.

In some embodiments, the liquid 122 can include a nutrient medium for the spores, such as a germination medium that will promote germination of surviving spores. In some embodiments, the liquid 122 can include water (or another solvent) that can be combined with nutrients to form a nutrient medium. Suitable nutrients can include nutrients necessary to promote germination and/or growth of surviving spores and may be provided in a dry form (e.g., powdered form, tablet form, caplet form, capsule form, a film or coating, entrapped in a bead or other carrier, another suitable shape or configuration, or a combination thereof) in the reservoir 103, for example, in a region of the biological sterilization indicator 100 near the spores 115.

The nutrient medium is generally selected to induce germination and initial outgrowth of the spores, if viable. The nutrient medium can include one or more sugars, including, but not limited to, glucose, fructose, cellibiose, or the like, or a combination thereof. The nutrient medium can also include a salt, including, but not limited to, potassium chloride, calcium chloride, or the like, or a combination thereof. In some embodiments, the nutrient can further include at least one amino acid, including, but not limited to, at least one of methionine, phenylalanine, and tryptophan.

In some embodiments, the nutrient medium can include indicator molecules, for example, indicator molecules having optical properties that change in response to germination or growth of the spores. Suitable indicator molecules can include, but are not limited to, pH indicator molecules, enzyme substrates, DNA binding dyes, RNA binding dyes, other suitable indicator molecules, or a combination thereof.

As shown in FIGS. 1-5, the biological sterilization indicator 100 can further include an insert 130. In some embodiments, the insert 130 can be adapted to hold or carry the container 120, such that the container 120 is held intact in a location separate from the spores 115 during sterilization. That is, in some embodiments, the insert 130 can include (or function as) a carrier 132 for the container 120, particularly, before the container 120 is broken during the activation step (i.e., the step in which the liquid 122 is released from the container 120 and introduced to the spores 115, which typically occurs after a sterilization process).

In some embodiments, the insert 130 can be further adapted to allow the container 120 to move in the housing 102, e.g., longitudinally with respect to the housing 102. Such movement can be provided by a connector 134. One example of a connector 134 is illustrated in FIGS. 1-5 and includes a living hinge or fold 135 to allow the connector 134 to be flexible. Other suitable structures that allow the container 120 to remain held by the carrier 132 and to be moved in the housing 102 can also be employed, such as a biasing element (e.g., a spring), a variable-length connecter (e.g., a telescoping connector), or the like, or combinations thereof.

In some embodiments, the insert 130 can be further adapted to house the spores 115. For example, as shown in FIGS. 1-5, in some embodiments, the insert 130 can include a spore reservoir 136, in which the spores 115 can be positioned, either directly or on a substrate. In embodiments employing a nutrient medium that is positioned to be mixed with the liquid 122 when it is released from the container 120, the nutrient medium can be positioned near or in the spore reservoir 136, and the nutrient medium can be mixed with (e.g., dissolved in) the water when the water is released from the container 120. By way of example only, in embodiments in which the nutrient medium is provided in a dry form, the dry form can be present within the reservoir 103, the spore reservoir 136, on a substrate for the spores, or a combination thereof. In some embodiments, a combination of liquid and dry nutrient media can be employed.

In some embodiments, the spores 115 can be positioned directly in the lower portion 114 of the housing 102, or the spores 115 can be positioned in a spore reservoir, such as the spore reservoir 136 (e.g., provided by the insert 130 in the embodiment illustrated in FIGS. 1-5). Whether the spores 115 are positioned directly in the lower portion 114 of the housing 102 or in a spore reservoir, such as the spore reservoir 136, the spores 115 can be provided in a variety of ways. In some embodiments, the spores 115 can be in a spore suspension that can be positioned in a desired location in the biological sterilization indicator 100 and dried down. In some embodiments, the spores 115 can be provided on a substrate (not shown) that can be positioned and/or secured in a desired location in the biological sterilization indicator 100. Some embodiments can include a combination of spores 115 provided in a dried down form and spores 115 provided on a substrate.

In some embodiments, the substrate can be positioned to support the spores 115 and/or to help maintain the spores 115 in a desired locus. Such a substrate can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a reflective material (e.g., a metal foil), a glass, a porcelain, a ceramic, a gel-forming material (e.g., guar gum), or combinations thereof. In addition, or alternatively, such a substrate can include or be coupled to a hydrophilic coating to facilitate bringing the liquid 122 into intimate contact with the spores 115 (e.g., when the liquid 122 employed is aqueous). In addition, or alternatively, such a hydrophilic coating can be applied to any fluid path positioned to fluidly couple the liquid 122 and the spores 115. In some embodiments, in addition to, or in lieu of a hydrophilic coating, a hydrophobic coating can be applied to other portions of the housing 102 (e.g., the lower portion 114 of the housing 102) and/or spore reservoir 136, such that the liquid 122 is preferentially moved into contact with the spores 115.

In some embodiments, the insert 130 does not include the spore reservoir 136. In some embodiments, the spore reservoir 136 is provided by the lower portion 114 of the housing 102 itself, and the spores 115 can be positioned in the lower portion 114, adsorbed to an inner surface or wall of the lower portion 114, or combinations thereof. In some embodiments, the spores 115 can be provided on a substrate that is positioned in the lower portion 114 of the housing 102. In some embodiments, the portion of the reservoir 103 that is defined at least partially by the upper portion 116 of the housing 102 can be referred to as a "first reservoir" 109 and the portion of the reservoir 103 that is defined at least partially by the lower portion 114 of the housing 102 can be referred to as a "second reservoir" 111, and the first reservoir 109 and the second reservoir 111 can be positioned in fluid communication with each other to allow a sterilant and the liquid 122 to move from the first reservoir 109 to the second reservoir 111. In some embodiments, the degree of fluid connection between the first reservoir 109 and the second reservoir 111 (e.g., the size of an opening, such as the opening 117, connecting the first reservoir 109 and the second reservoir 111) can increase after, simultaneously with, and/or in response to the activation step (i.e., the liquid 122 being released from the container 120). In some embodiments, the control of fluid communication (or extent of fluid connection) between the first reservoir 109

(e.g., the upper portion 116) and the second reservoir 111 (e.g., the lower portion 114) can be provided by at least a portion of the insert 130.

Figure 3:
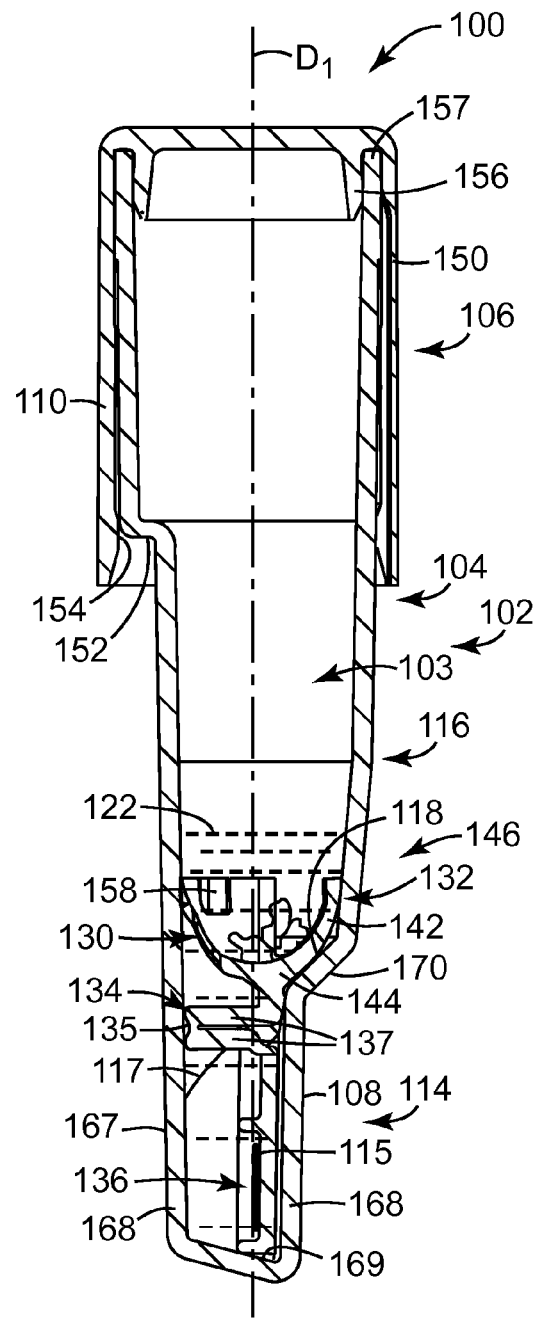
FIG. 3 is a side cross-sectional view of the biological sterilization indicator of FIGS. 1 and 2, after activation.

As shown in FIGS. 2 and 3, the second portion 106 of the housing 102 can be adapted to be coupled to the first portion 104. For example, as illustrated in FIGS. 1-4, the second portion 106 can be adapted to be coupled to the upper portion 116 of the first portion 104 of the housing 102. In some embodiments, as shown in FIGS. 1-4, the second portion 106 can be in the form of a cap that can be dimensioned to receive at least a portion of the first portion 104 of the housing 102.

As shown in FIG. 2, during sterilization and before activation, the second portion 106 can be in a first position 148 with respect to the first portion 104. As shown in FIG. 3, after sterilization, the biological sterilization indicator 100 can be activated to release the liquid 122 from the container 120 to move the liquid 122 to the spores 115. That is, the second portion 106 of the housing 102 can be moved to a second position 150 with respect to the first portion 104. By way of example only, in the embodiment illustrated in FIGS. 1-4, the first portion 104 of the housing 102 includes a step or overhang 152 in its outer surface, and the second portion 106 includes a lip or protrusion 154 that can be adapted to engage with the step 152 on the first portion 104 when the second portion 106 is moved from the first position 148 to the second position 150. In such embodiments, the second portion 106 can reversibly engage the first portion 104 in the second position 150, and in some embodiments, the second portion 106 can irreversibly engage the first portion 104.

A variety of coupling means can be employed between the first portion 104 and the second portion 106 of the housing 102 to allow the first portion 104 and the second portion 106 to be removably coupled to one another, including, but not limited to, gravity (e.g., one component can be set atop another component, or a mating portion thereof), screw threads, press-fit engagement (also sometimes referred to as "friction-fit engagement" or "interference-fit engagement"), snap-fit engagement, magnets, adhesives, heat sealing, other suitable removable coupling means, and combinations thereof. In some embodiments, the biological sterilization indicator 100 need not be reopened and the first portion 104 and the second portion 106 need not be removably coupled to one another, but rather can be permanently or semi-permanently coupled to one another. Such permanent or semi-permanent coupling means can include, but are not limited to, adhesives, stitches, staples, screws, nails, rivets, brads, crimps, welding (e.g., sonic (e.g., ultrasonic) welding), any thermal bonding technique (e.g., heat and/or pressure applied to one or both of the components to be coupled), snap-fit engagement, press-fit engagement, heat sealing, other suitable permanent or semi-permanent coupling means, and combinations thereof. One of ordinary skill in the art will recognize that some of the permanent or semi-permanent coupling means can also be adapted to be removable, and vice versa, and are categorized in this way by way of example only.

In the embodiment illustrated in FIGS. 1-4, the second portion 106 is shown as being movable between a first longitudinal position 148 with respect to the first portion 104 and a second longitudinal position 150 with respect to the first portion 104; however, it should be understood that the biological sterilization indicator 100 could instead be configured differently, such that the first and second positions 148 and 150 are not necessarily longitudinal positions with respect to one or both of the first portion 104 and the second portion 106 of the housing 102.

The second portion 106 can further include a seal 156 (e.g., a projection, a protrusion, a flap, flange, o-ring, or the like, or combinations thereof) that can be positioned to contact an open upper end 157 of the first portion 104 of the housing 102 to close or seal (e.g., hermetically seal) the biological sterilization indicator 100 after the second portion 106 has been moved to the second position 150, and the liquid 122 has been released from the container 120. The seal 156 can take a variety of forms and is shown in FIGS. 2 and 3 by way of example as forming an inner ring that together with the wall 110 of the second portion 106 is dimensioned to receive the upper end 157 of the first portion 104 of the housing 102 to seal the biological sterilization indicator 100.

In some embodiments, the coupling between the seal 156 and the upper end 157 of the first portion 104 of the housing 102 can be used in addition to, or in lieu of, the coupling between the step 152 and the protrusion 154 described above. For example, one or both of the seal 156 and the upper end 157 can further include a structure (e.g., a protrusion) configured to engage the other of the upper end 157 and the seal 156, respectively, in order to couple the second portion 106 of the housing 102 to the first portion 104 of the housing 102.

In addition, in some embodiments, the second portion 106 of the housing 102 can be coupled to the first portion 104 of the housing 102 (e.g., by the step 152 and the protrusion 154 and/or the seal 156 and the upper end 157 of the first portion 104 of the housing 102) to seal the biological sterilization indicator 100 from ambience after activation. Such sealing can inhibit contamination or spilling of the liquid 122 after it has been released from the container 120, and/or can inhibit contamination of the interior of the biological sterilization indicator 100.

Figure 5:
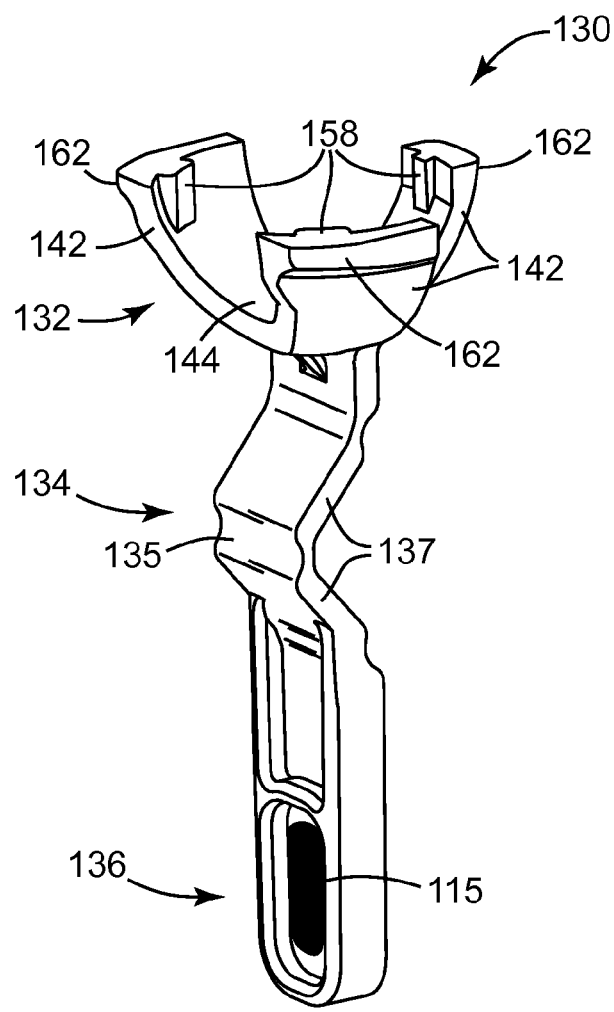
FIG. 5 is a perspective view of the insert of FIGS. 1-4.

The insert 130 will now be described in greater detail, with particular reference to FIG. 5. As shown in FIG. 5 and mentioned above, in some embodiments, the insert 130 can include a carrier 132. In the embodiment illustrated in FIGS. 1-5, the carrier 132 includes three arms 142 that are connected together via a cup-shaped base 144, and the arms 142 and the base 144 are shaped and dimensioned to cradle a portion of the container 120. By way of example only, the arms 142 and the base 144 are illustrated as being shaped and dimensioned to hold the bottom of a container 120 having a round end; however, it should be understood that the carrier 132 can instead be configured to hold a container 120 having a different shape.

In some embodiments, as shown in FIGS. 1-5, the carrier 132 can be movable (e.g., longitudinally) in the housing 102, for example, in response to the second portion 106 of the housing 102 being moved from its first position 148 to its second position 150. That is, as shown in FIGS. 2 and 3, the carrier 132 can include a first position (e.g., a first longitudinal position) in which the container 120 is not fractured, and a second position (e.g., a second longitudinal position) in which the container 120 is fractured. The first position of the carrier 132 can correspond to the first position 148 of the second portion 106 of the housing 102, and the second position of the carrier 132 can correspond to the second position 150 of the second portion 106 of the housing 102.

At least a portion of the arms 142 can be formed of a flexible material, such that the arms 142 can move or flex, for example, in response to the carrier 132 being moved in the housing 102. For example, in the embodiment illustrated in FIGS. 1-5, at least a portion of the housing 102 (e.g., the first portion 104) can include a tapered portion 146 in which the housing 102 (e.g., at least an inner surface of the wall 108) generally tapers in the longitudinal direction $D_1$. As a result, the cross-sectional area in the housing 102 can generally decrease along the longitudinal direction $D_1$. In the embodiment illustrated in FIGS. 1-4, the tapered portion 146 is shown as being a result of the entire wall 108 tapering. However, it should be understood that the inner dimensions of the housing 102 can generally decrease in the tapered portion along the longitudinal direction $D_1$ without the outer dimensions of the housing 102 changing. In some embodiments, the outer dimensions of the housing 102 can be uniform along its length, even though the inner portion of the housing 102 tapers along its length.

In the embodiment illustrated in FIGS. 1-5, as the second portion 106 of the housing 102 is moved from the first position 148 (see FIG. 2) to the second position 150 (see FIG. 3), the second portion 106 contacts (e.g., directly or indirectly) the container 120, causing the container 120 to move longitudinally downwardly in the tapered portion 146 the housing 102, for example, by virtue of the connector 134 of the insert 130. As the container 120 is moved in the housing 102, the cross-sectional area available to the carrier 132 and the container 120 decreases, causing the arms 142 of the carrier 132 to squeeze the container 120 and impinge on an outer surface of the container 120.

In some embodiments, as shown in FIG. 5, the insert 130 can further include one or more ribs or projections 158 positioned to concentrate the crushing force to increase the pressure on the container 120 in the regions adjacent the projections 158, and to facilitate fracturing the container 120 more easily and in one or more desired regions. The projections 158 can also function at least partially to hold a portion of the container 120, and the projections 158 can reduce the total effort or force needed to move the second portion 106 between the first position 148 and the second position 150, and to fracture the container 120 (or a portion thereof).

In some embodiments, the arms 142 of the insert 130 can be movable inwardly/outwardly (e.g., radially inwardly/outwardly) with respect to the outer surface of the container 120, for example, in response to moving the carrier 132 longitudinally in the housing 102 in response to moving the second portion 106 of the housing 102 between its first position 148 and its second position 150. Such flexibility in the arms 142 can facilitate squeezing or crushing the container 120. In some embodiments, as shown in FIG. 5, one or more of the arms 142 can include an outer projection 162 positioned to contact an inner surface of the wall 108 (or of the first portion 104 of the housing 102) and cam along the surface as the second portion 106 of the housing 102 is moved between the first position 148 and the second position 150. Such camming action can further control and facilitate movement of the container 120 in the housing and/or fracturing of the container 120. In some embodiments, the first position of one or more of the arms 142 (and the projections 158) can correspond to the first position 148 of the second portion 106 of the housing 102 (and/or the first position of the carrier 132). In addition, in some embodiments, the second position of one or more of the arms 142 (and the projections 158) can correspond to the second position 150 of the second portion 106 of the housing 102 (and/or the second position of the carrier 132).

As shown in FIGS. 2 and 3, the arms 142 (and anything coupled to the arms 142, such as the projections 158) can be movable radially toward and away from the outer surface of the container 120, between a first position (e.g., a first radial position) in which the projections 158 are not fracturing, or possibly even contacting, the container 120, and a second position (e.g., a second radial position) in which the projections 158 are fracturing the container 120.

In some embodiments, at least a portion of the insert 130 can be or include a "breaker," and can be adapted to break or open the container 120 to release the liquid 122. For example, in some embodiments, the projections 158 (or the projections 158 in combination with another portion of the insert 130, such as the carrier 132 and/or the arms 142) can be referred to as the "breaker" of the biological sterilization indicator 100.

As shown in FIGS. 1-5, and particularly, in FIG. 5, the carrier 132 is configured to hold a bottom portion of the container 120, and the arms 142 and projections 158 are positioned to fracture the container 120 at a location near the bottom of the container 120 as its positioned in the housing 102. Such a configuration can allow the container 120 to be broken near its bottom and can facilitate removal of the liquid 122 from the container 120, which can enhance the availability of the liquid 122 to the spores 115, and can enhance the reliability of releasing the liquid 122 into fluid communication with the spores 115 (e.g., with the spore reservoir 136). Such a configuration is shown by way of example only, however, and it should be understood that the arms 142 can be shorter or longer than illustrated and the projections 158 can be positioned higher or lower than illustrated in order to fracture the container 120 in any desired manner.

In some embodiments, the insert 130 does not include the ribs or projections 158 positioned to concentrate the crushing force on the container 120, but rather, the arms 142 themselves squeeze and fracture the container 120 as the second portion 106 is moved from the first position 148 to the second position 150. The container 120 is shown as being an oblong capsule or ampoule with two hemispherical or radiused ends connected by flat, substantially straight sidewalls. In such container embodiments, the arms 142 (whether the arms 142 include the projections 158 or not), as shown in FIGS. 1-5, can be configured to extend far enough around an end of the container 120, such that the arms 142 are positioned to fracture the container 120 in a position on its flat wall, for example, where the container 120 may be weakest. For example, the arms 142 and/or the projections 158 can be configured to contact the container 120 in a direction that is substantially perpendicular to the flat side of the container 120. Such embodiments can reduce the overall breaking force (and activation force) required to fracture the container 120. The oblong capsule-shaped container 120 is shown by way of example only, however, it should be understood that a variety of container configurations can be employed, and the insert 130 and carrier 132 can be configured to operate with any container shape. In some embodiments, the carrier 132 can be configured to fracture the container 120 at a radiused end. For example, the embodiments illustrated in FIGS. 6-7, 8-9, 10-13 and 14-17 each include inserts (and carriers) adapted to fracture a container at its radiused end.

In some embodiments, the base 144 of the carrier 132 can be configured to facilitate movement of the liquid 122 to the spores 115 after the container 120 has been fractured. For example, in some embodiments, the base 144 can include an aperture or the majority of the base can include an aperture that is positioned to facilitate movement of the liquid 122 past the carrier 132 after the container 120 has been fractured.

In some embodiments, as shown in FIG. 2, the insert 130 can be sized and shaped to allow the container 120 to be held out of the tapered portion 146 of the housing 102 during sterilization and before activation to inhibit accidental or premature activation of the biological sterilization indicator 100. Such a configuration can also inhibit inadvertent breakage due to shock or material expansion (e.g., due to exposure to heat during a sterilization process).

In the embodiment illustrated in FIGS. 1-5, the insert 130 includes three arms 142 that are equally spaced circumferentially about the container 120. However, this need not be the case. In some embodiments, one arm 142 is sufficient both to hold the container 120 before activation and to fracture the container 120 as the second portion 106 of the housing 102 is moved to the second position 150. In some embodiments, a combination of elements on the insert 130 and elements on the housing 102 (e.g., on the wall 108 of the first portion 104) can be employed to hold and/or fracture the container 120.

As shown in FIGS. 2 and 4, whether the insert 130 includes one or more arms 142, the arms 142 (e.g., themselves or in combination with a portion of the housing 102) can be configured to hold the container 120 in the housing 102 in a consistent location to provide a substantially constant sterilant path 164 during sterilization. For example, rather than allowing the container 120 to move or roll around (e.g., radially and/or longitudinally) in the housing 102 before activation (e.g., during sterilization), the insert 130 can hold the container 120 in a substantially consistent position, which can allow a sterilant a substantially consistent and relatively unobstructed path between an outer surface of the container 120 and an inner surface of the housing 102, with little or no opportunity for inadvertent blockage.

As shown in FIG. 4, the arms 142 need not all be the exact same shape or size and can be sized and positioned to control the sterilant path 164, for example to tailor the kill/survival rate of the biological sterilization indicator 100, to inhibit inadvertent fracture of the container 120, to facilitate movement of the container 120 in the housing 120, to mate with or engage the housing 102, and/or to control the breakage of the container 120.

As shown in FIG. 2, in the first position 148, the container 120 can be held intact in a position separate from the lower portion 114 or the spore reservoir 136, and the liquid 122 can be contained within the container 120. In addition, in the first position 148, as shown in FIG. 4, the insert 130, and particularly, the carrier 132, can be used to hold the container 120 in a position in the housing 102 in which a minimal cross-sectional area of the space between the container 120 and the housing 102 and/or between the container 120 and any other structures or components positioned in the housing 102 (e.g., at least a portion of the insert 130, such as the carrier 132, etc.) is maintained.

In some cases, without providing the means to maintain at least a minimal spacing around the container 120 (e.g., between the container 120 and surrounding structure), there can be a possibility that the container 120 can become positioned in the housing 102 (e.g., in the tapered portion 146) in such a way that it obstructs or blocks the sterilant path 164. However, the biological sterilization indicator 100 of the present disclosure is designed to inhibit this from occurring. For example, in the embodiment illustrated in FIGS. 1-5, the insert 130 (and particularly, the carrier 132) can be configured to hold the container 120 out of the tapered portion 146 of the housing 102, such that at least a minimal cross-sectional area is maintained around the container 120 in any orientation of the biological sterilization indicator 100 prior to activation. For example, in the embodiment illustrated in FIGS. 1-5, even if the biological sterilization indicator 100 is tipped upside down, the container 120 may fall away from contact with the insert 130, but in no orientation, is the container 120 moved any closer to the tapered portion 146, or the spores 115 until activation of the biological sterilization indicator 100. In addition, until activation, at least a minimal spacing (and particularly, a cross-sectional area of that spacing) between the container 120 and the housing 102 and/or the insert 130 can be maintained to provide a substantially constant sterilant path 164, for example, around the container 120.

In some embodiments, the relative sizing and positioning of the components of the biological sterilization indicator 100 can be configured such that, before activation, the container 120 is held intact in a substantially consistent location in the biological sterilization indicator 100. Such a configuration can provide a substantially constant sterilant path 164 and can maintain the container 120 in a position such that the container 120 is not able to move substantially, if at all, in the biological sterilization indicator 100 before activation.

With reference to FIGS. 2, 3 and 5, and as mentioned above, the connector 134 can include one or more hinges or folds 135. The connector 134 can further include one or more sections 137 adjacent the hinge 135 that can be movable toward or away from each other (e.g., open or collapsed) as the hinge 135 is opened or closed. As shown in FIG. 2, before activation, the hinge 135 can be relatively open or expanded, such that the sections 137 adjacent the hinge 135 are separated a first amount. As shown in FIG. 3, after activation, the hinge 135 can be relatively closed or collapsed, such that the sections 137 adjacent the hinge 135 are separated a second, lesser, amount. That is, as shown in FIG. 2, before activation, the connector 134 can have a first configuration, and, as shown in FIG. 3, after activation, the connector 134 can have a second configuration.

As further shown in FIG. 3, in the second configuration of the connector 134, the sections 137 of the connector 134 can be collapsed upon one another and can be positioned to substantially block or close the opening 117 between the upper portion 116 and the lower portion 114 of the housing 102. This second configuration of the connector 134 can inhibit broken portions of the container 120 (e.g., shards) from moving downstream in the biological sterilization indicator 100 into the lower portion 114 of the housing 102 where the portions of the container 120 could interfere with spore growth and/or detection of spore growth. As shown in FIG. 3, the base 144 of the carrier 132 can also collect or retain portions of the container 120 to inhibit such portions from moving downstream in the housing 102.

In addition, the second configuration of the connector 134 can inhibit diffusion of the spores 115 and/or one or more detection signals out of the lower portion 114 of the housing 102, which can enhance detection of any spore growth. For example, in some embodiments, spore growth is determined by fluorescent indicators/molecules (e.g., fluorophores) or other markers. In some embodiments, if the liquid level after activation in the biological sterilization indicator 100 is above the location of the spores 115, such molecules or markers, or the spores 115 themselves, can move or diffuse away from or out of the spore reservoir 136 and, potentially, out of the lower portion 114 of the housing 102.

In some embodiments, at least a portion of the housing 102, for example, the lower portion 114 of the housing 102, can be transparent to an electromagnetic radiation wavelength or range of wavelengths (e.g., when optical detection methods are employed), which can facilitate detection of spore growth. That is, in some embodiments, at least a portion of the housing 102 can include or form a detection window 167.

In addition, in some embodiments, as shown in FIGS. 1-5, at least a portion of the housing 102, for example, the lower portion 114 can include one or more planar walls 168. Such planar walls 168 can facilitate detection (e.g., optical detection) of spore growth. In addition, in the embodiment illustrated in FIGS. 1-5, the wall 108 of the first portion 104 of the housing 102 can include one or more stepped regions, such as the step 152 described above and a tapered wall or step 170. The tapered wall 170 can function to reduce the overall thickness and size of the lower portion, or detection portion, 114 of the housing 102, which can facilitate detection. In addition, having one or more steps and/or tapered walls 152, 170 can allow the biological sterilization indicator 100 to be coupled to a reader or detection device in only one orientation, such that the biological sterilization indicator 100 is "keyed" with respect to a reader, which can minimize user error and enhance reliability of a detection process.

By way of example only, the insert 130 illustrated in FIGS. 1-5 is shown as being a unitary device that includes at least the following: means for holding the container 120 before activation, for fracturing the container 120 during activation; for allowing movement of the container 120 in the housing 102; for providing a substantially constant sterilant path 164, for providing a spore reservoir 136; for collecting and/or retaining portions of the fractured container 120 after activation (or at least partially inhibiting movement of portions of the fractured container 120 into the lower portion 114 of the housing 102); and/or for minimizing diffusion of the spores 115 and/or signals from the lower portion 114 to the upper portion 116 of the housing 102 after activation. However, it should be understood that in some embodiments, the insert 130 can include multiple portions that may not be part of a single, unitary device, and each of the portions can be adapted to do one or more of the above functions.

The unitary configuration of the insert 130 can also facilitate the movement of the container 120 in the housing 102. For example, because the insert 130 extends from the location where it supports the container 120 all the way to the base of the reservoir 103 in the housing 102, the bottom of the insert 130 can press against a base 169 of the housing 102 as the second portion 106 is moved from the first position 148 to the second position 150. By allowing the insert 130 to extend all the way to the base 169 of the housing 102, the necessary resistance and force can be obtained to allow the carrier 132 (and the container 120) to move in the housing 102 with respect to the spore reservoir 136 and the lower portion 114 of the housing 102, and/or to fracture the container 120. However, it should be understood that other configurations are possible and can be employed. For example, in some embodiments, such as the embodiment illustrated in FIGS. 10-13 and described below, the insert 130 can be configured to abut the separating wall 118 to provide the necessary resistance and force to fracture the container 120.

In addition, the insert 130 is referred to as an "insert" because in the embodiment illustrated in FIGS. 1-5, the device that performs the above functions is a device that can be inserted into the reservoir 103 of the housing 102. However, it should be understood that the insert 130 can instead be provided by the housing 102 itself or another component of the biological sterilization indicator 100 and need not necessarily be insertable into the housing 102. The term "insert" will be described throughout the present disclosure for simplicity, but it should be understood that such a term is not intended to be limiting, and it should be appreciated that other equivalent structures that perform one or more of the above functions can be used instead of, or in combination with, the insertable insert 130. Furthermore, in the embodiment illustrated in FIGS. 1-5, the insert 130 is both insertable into and removable from the housing 102, and particularly, into and out of the first portion 104 of the housing 102. However, it should be understood that even if the insert 130 is insertable into the housing 102, the insert 130 need not be removable from the housing 102, but rather can be fixedly coupled to the housing 102 in a manner that inhibits removal of the insert 130 from the housing 102 after positioning the insert 130 in a desired location.

The biological sterilization indicator of the present disclosure generally keeps the liquid 122 and the spores 115 separate but in relatively close proximity (e.g., within the self-contained biological sterilization indicator 100) during sterilization, such that the liquid 122 and the spores 115 can be readily combined after exposure to a sterilization process. The liquid 122 and the spores 115 can be incubated during a detection process, or the biological sterilization indicator 100 can be incubated prior to a detection process. In some embodiments, when incubating the spores with the liquid 122, an incubation temperature above room temperature can be used. For example, in some embodiments, the incubation temperature is at least about 37° C., in some embodiments, the incubation temperature is at least about 50° C. (e.g., 56° C.), and in some embodiments, at least about 60° C. In some embodiments, the incubation temperature is no greater than about 60° C., in some embodiments, no greater than about 50° C., and in some embodiments, no greater than about 40° C.

A detection process can be adapted to detect a detectable change from the spores (e.g., from within the spore reservoir 136). That is, a detection process can be adapted to detect a variety of characteristics, including, but not limited to, electromagnetic radiation (e.g., in the ultraviolet, visible, and/or infrared bands), fluorescence, luminescence, light scattering, electronic properties (e.g., conductance, impedance, or the like, or combinations thereof), turbidity, absorption, Raman spectroscopy, ellipsometry, or the like, or a combination thereof. Detection of such characteristics can be carried out by one or more of a fluorimeter, a spectrophotometer, colorimeter, or the like, or combinations thereof. In some embodiments, such as embodiments that measure fluorescence, visible light, etc., the detectable change is measured by detecting at a particular wavelength.

The spores and/or the liquid 122 can be adapted (e.g., labeled) to produce one or more of the above characteristics as a result of a biochemical reaction that is a sign of spore viability. As a result, no detectable change (e.g., as compared to a baseline or background reading) can signify an effective sterilization process, whereas a detectable change can signify an ineffective sterilization process. In some embodiments, the detectable change can include a rate at which one or more of the above characteristics is changing (e.g., increasing fluorescence, decreasing turbidity, etc.).

In some embodiments, spore viability can be determined by exploiting enzyme activity. As described in Matner et al., U.S. Pat. No. 5,073,488, entitled "Rapid Method for Determining Efficacy of a Sterilization Cycle and Rapid Read-out Biological Indicator," which is incorporated herein by reference, enzymes can be identified for a particular type of spore in which the enzyme has particularly useful characteristics that can be exploited to determine the efficacy of a sterilization process. Such characteristics can include the following: (1) the enzyme, when subjected to sterilization conditions which would be sufficient to decrease a population of $1\times10^6$ test microorganisms by about 6 logs (i.e., to a population of about zero as measured by lack of outgrowth of the test microorganisms), has a residual activity which is equal to "background" as measured by reaction with a substrate system for the enzyme; and (2) the enzyme, when subjected to sterilization conditions sufficient only to decrease the population of $1\times10^6$ test microorganisms by at least 1 log, but less than 6 logs, has enzyme activity greater than "background" as measured by reaction with the enzyme substrate system. The enzyme substrate system can include a substance, or mixture of substances, which is acted upon by the enzyme to produce a detectable enzyme-modified product, as evident by a detectable change.

In some embodiments, the biological sterilization indicator 100 can be assayed in a single-side mode, where the biological sterilization indicator 100 includes only one detection window (e.g., detection window 167 of FIG. 1) that is positioned, for example, near the spores 115. In some embodiments, however, the biological sterilization indicator 100 can include more than one detection window (e.g., a window formed by all or a portion of both parallel walls 168 of the lower portion 114 of the housing 102), such that the biological sterilization indicator 100 can be assayed via more than one detection window. In embodiments employing multiple detection windows, the detection windows can be positioned side-by-side (similar to a single-side mode), or the detection windows can be oriented at an angle (e.g., 90 degrees, 180 degrees, etc.) with respect to one another.

In general, the spores 115 are positioned within the spore reservoir 136 which is in fluid communication with the reservoir 103. In some embodiments, the spore reservoir 136 forms a portion of the reservoir 103. As shown in FIG. 2, the reservoir 103 is in fluid communication with ambience (e.g., via the aperture 107) during sterilization to allow sterilant to enter the reservoir 103 during a sterilization process to sterilize the spores 115. The container 120 can be configured to contain the liquid 122 during sterilization to inhibit the liquid 122 from being in fluid communication with the spores 115, the reservoir 103, and the sterilant during sterilization.

In some embodiments, the spores 115 can be positioned in one locus of spores or in a plurality of loci of spores, all of which can be positioned either in the reservoir 103, in the lower portion 114 of the housing 102, and/or in the spore reservoir 136. In some embodiments, having multiple loci of spores can maximize the exposure of the spores to sterilant and to the liquid 122, can improve manufacturing (e.g., placement of the spores can be facilitated by placing each locus of spores in a depression within the biological sterilization indicator 100), and can improve detection characteristics (e.g., because spores in the middle of one large locus of spores may not be as easily detected). In embodiments employing a plurality of loci of spores, each locus of spores can include a different, known number of spores, and/or each locus of spores can include different spores, such that a plurality of spore types can be tested. By employing multiple types of spores, the biological sterilization indicator 100 can be used for a variety of sterilization processes and a specific locus of spores can be analyzed for a specific sterilization process, or the multiple types of spores can be used to further test the effectiveness, or confidence, of a sterilization process.

In addition, in some embodiments, the biological sterilization indicator 100 can include a plurality of spore reservoirs 136, and each spore reservoir 136 can include one or more loci of spores 115. In some embodiments employing a plurality of spore reservoirs 136, the plurality of spore reservoirs 136 can be positioned in fluid communication with the reservoir 103.

In some embodiments, the spores 115 can be covered with a cover (not shown) adapted to fit in or over the spore reservoir 136. Such a cover can help maintain the spores within the desired region of the biological sterilization indicator 100 during manufacturing, sterilization and/or use. The cover, if employed, can be formed of a material that does not substantially impede a detection process, and/or which is at least partially transmissive to electromagnetic radiation wavelengths of interest. In addition, depending on the material makeup of the cover, in some embodiments, the cover can facilitate wicking the liquid 122 (e.g., the nutrient medium) along the spores 115. In some embodiments, the cover can also contain features for facilitating fluid flow into the spore reservoir 136, such as capillary channels, hydrophilic microporous fibers or membranes, or the like, or a combination thereof In addition, in some embodiments, the cover can isolate a signal, or enhance the signal, which can facilitate detection. Such a cover can be employed whether the spores 115 are positioned within the spore reservoir 136 or directly in the lower portion 114 of the housing 102. In addition, such a cover can be employed in embodiments employing a plurality of loci of spores. The cover can include a variety of materials, including, but not limited to, paper, a polymer (e.g., any of the polymers listed above with respect to the housing 102), an adhesive (e.g., acrylate, natural or synthetic rubber, silicone, silicone polyurea, isocyanate, epoxy, or combinations thereof), a woven cloth, a nonwoven cloth, a microporous material (e.g., a microporous polymeric material), a glass, a porcelain, a ceramic, a gel-forming material (e.g., guar gum), or combinations thereof In some embodiments, the biological sterilization indicator 100 can further include a modified inner surface, such as a reflective surface, a white surface, a black surface, or another surface modification suitable to optimize the optical properties of the surface. A reflective surface (e.g., provided by a metal foil) can be positioned to reflect a signal sent into the spore reservoir 136 from an assaying or detection device and/or to reflect any signal generated within the spore reservoir 136 back toward the assaying device. As a result, the reflective surface can function to improve (e.g., improve the intensity of) a signal from the biological sterilization indicator 100. Such a reflective surface can be provided by an inner surface of the housing 102; a material coupled to the inner surface of the housing 102; an inner surface the spore reservoir 136; a material coupled to the inner surface of the spore reservoir 136; or the like; or the reflective surface can form a portion of or be coupled to a spore substrate; or a combination thereof Similarly, in some embodiments, the biological sterilization indicator 100 can further include a white and/or black surface positioned to increase and/or decrease a particular signal sent into the spore reservoir 136 from an assaying device and/or to increase and/or decrease a particular signal generated within the spore reservoir 136. By way of example only, a white surface can be used to enhance a signal, and a black surface can be used to reduce a signal (e.g., noise).

In some embodiments, the spores 115 can be positioned on a functionalized surface to promote the immobilization of the spores 115 on the desired surface. For example, such a functionalized surface can be provided by an inner surface of the housing 102, can be provided by an inner surface of the spore reservoir 136, can form a portion of or be coupled to a spore substrate, or the like, or a combination thereof.

In some embodiments, the spores 115 are positioned (e.g. applied by coating or another application method) on a microstructured or microreplicated surface (e.g., such microstructured surfaces as those disclosed in Halverson et al., PCT Publication No. WO 2007/070310, Hanschen et al., US. Publication No. US 2003/0235677, and Graham et al., PCT Publication No. WO 2004/000569, all of which are incorporated herein by reference). For example, such a microstructured surface can be provided by an inner surface of the housing 102, an inner surface of the spore reservoir 136, form a portion of or be coupled to a spore substrate, or the like, or a combination thereof.

In some embodiments, the biological sterilization indicator 100 can further include a gel-forming material positioned to be combined with the spores 115 and the liquid 122 when the liquid 122 is released from the container 120. For example, the gel-forming material can be positioned near the spores 115 (e.g., in the spore reservoir 136), in the lower portion 114 of the housing 102, can form a portion of or be coupled to a spore substrate, or the like, or a combination thereof. Such a gel-forming material can form a gel (e.g., a hydrogel) or a matrix comprising the spores and nutrients when the liquid 122 comes into contact with the spores. A gel-forming material (e.g., guar gum) can be particularly useful because it has the ability to form a gel upon hydration, it can aid in localizing a signal (e.g., fluorescence), it can anchor the spores 115 in place, it can help minimize diffusion of the spores 115 and/or a signal from the spore reservoir 136, and it can enhance detection.

In some embodiments, the biological sterilization indicator 100 can further include an absorbent or a wicking material. For example, the wicking material can be positioned near the spores 115 (e.g., in the spore reservoir 136), can form at least a portion of or be coupled to a spore substrate, or the like, or a combination thereof. Such a wicking material can include a porous wicking pad, a soaking pad, or the like, or a combination thereof, to facilitate bringing the liquid 122 into intimate contact with the spores.

In some embodiments, the frangible container 120 can be configured to facilitate fracturing of the frangible container 120 in a desired manner. For example, in some embodiments, a lower portion of the frangible container 120 can be formed of a thinner and/or weaker material, such that the lower portion preferentially fractures over another portion of the frangible container 120. In addition, in some embodiments, the frangible container 120 can include a variety of features positioned to facilitate fracturing of the frangible container 120 in a desired manner, including, but not limited to, a thin and/or weakened area, a score line, a perforation, or the like, or combinations thereof.

As a result, the frangible container 120 has a first closed state in which the liquid 122 is contained within the frangible container 120 and a second open state in which the frangible container 120 has fractured and the liquid 122 is released into the reservoir 103 and/or the spore reservoir 136, and into contact with the spores 115.

In some embodiments, the biological sterilization indicator 100 can be activated (e.g., the second portion 106 can be moved to the second position 150) manually. In some embodiments, the biological sterilization indicator 100 can be activated by a reader or assaying device (e.g., by positioning the biological sterilization indicator 100 in the reader or assaying device). In some embodiments, the biological sterilization indicator 100 can be activated with a device independent of the assaying device or reader (e.g., by positioning the biological sterilization indicator 100 in the device). In some embodiments, the biological sterilization indicator 100 can be activated by a combination of two or more of the assaying device, a device independent of the assaying device, and manual activation.

One or both of the biological sterilization indicator 100 and another device, such as an assaying device can be further configured to inhibit premature or accidental fracturing of the frangible container 120. For example, in some embodiments, the biological sterilization indicator 100 can include a lock or locking mechanism that is positioned to inhibit the second portion 106 of the housing 102 from moving into the second position 150 until desired. In such embodiments, the biological sterilization indicator 100 cannot be activated until the lock is moved, removed or unlocked. In addition, or alternatively, in some embodiments, the biological sterilization indicator 100 can include a lock or locking mechanism that is positioned to inhibit the second portion 106 of the housing 102 from moving from the second position 150 back into the first position 148 after activation.

In some embodiments, the reservoir 103 has a volume of at least about 0.5 milliliters (mL), in some embodiments, at least about 1 mL, and in some embodiments, at least about 1.5 mL. In some embodiments, the reservoir 103 has a volume of no greater than about 5 mL, in some embodiments, no greater than about 3 mL, and in some embodiments, no greater than about 2 mL.

In some embodiments, the spore growth chamber 114 (i.e., the lower portion 114 of the first portion 104 of the housing 102) has a volume of at least about 5 microliters, in some embodiments, at least about 20 microliters, and in some embodiments, at least about 35 microliters. In some embodiments, the spore growth chamber 114 has a volume of no greater than about 250 microliters, in some embodiments, no greater than about 175 microliters, and in some embodiments, no greater than about 100 microliters.

In some embodiments, the spore reservoir 136 has a volume of at least about 1 microliter, in some embodiments, at least about 5 microliters, and in some embodiments, at least about 10 microliters. In some embodiments, the spore reservoir 136 has a volume of no greater than about 250 microliters, in some embodiments, no greater than about 175 microliters, and in some embodiments, no greater than about 100 microliters.

In some embodiments, the frangible container 120 has a volume of at least about 0.25 mL, in some embodiments, at least about 0.5 mL, and in some embodiments, at least about 1 mL. In some embodiments, the frangible container 120 has a volume of no greater than about 5 mL, in some embodiments, no greater than about 3 mL, and in some embodiments, no greater than about 2 mL.

In some embodiments, the volume of the liquid 122 contained in the frangible container 120 is at least about 50 microliters, in some embodiments, at least about 75 microliters, and in some embodiments, at least about 100 microliters. In some embodiments, the volume of the liquid 122 contained in the frangible container 120 is no greater than about 5 mL, in some embodiments, no greater than about 3 mL, and in some embodiments, no greater than about 2 mL.

In some embodiments, as shown in FIGS. 1-4, at least a portion of the housing can be flat (e.g., the parallel walls 168), and can be substantially planar with respect to the spore reservoir 136, and one or both of the parallel walls 168 or a portion thereof (e.g., the detection window 167) can be sized such that at least one dimension of the wall 168 (or detection window 167) substantially matches at least one dimension of the spore reservoir 136 and/or the locus of spores 115. Said another way, the wall 168 or a portion thereof (e.g., the detection window 167) can include a cross-sectional area that is substantially the same size as the cross-sectional area of the spore reservoir 136 and/or the locus of spores 115. Such size matching between the wall 168/detection window 167 and the spore reservoir 136 and/or the locus of spores 115 can maximize the signal detected during a detection or assaying process. Alternatively, or in addition, the wall 168 or detection window 167 can be sized to match the reservoir 103 (e.g., at least one dimension or the cross-sectional areas can be sized to match). Such size matching between detection zones can improve spore assaying and detection.

The biological sterilization indicator 100 illustrated in FIGS. 1-4, at least the portion of the biological sterilization indicator 100 where the spores 115 are positioned, is relatively thin (i.e., the "z dimension" is minimized), such that an optical path from the spores to the wall 168 (or detection window 167) is minimized and/or any effect of interfering substances in the liquid 122 (or nutrient medium) is minimized.

In use, the biological sterilization indicator 100 can be placed along with a sterilizing batch for a sterilization process. During sterilization, a sterilant is in fluid communication with the reservoir 103, the spore reservoir 136, and the spores 115 primarily via the sterilant path 164, such that sterilant can reach the spores to produce sterilized spores. In addition, during sterilization, the frangible container 120 is in a closed state in which the liquid 122 is protected from the sterilant and is not in fluid communication with the reservoir 103, the spore reservoir 136, the spores 115, or the sterilant path 164.

Following sterilization, the effectiveness of the sterilization process can be determined using the biological sterilization indicator 100. The second portion 106 of the housing 102 can be unlocked, if previously locked in the first position 148, and moved from the first position 148 to the second position 150. Such movement of the second portion 106 can cause the connector 134 of the insert 130 to flex at the hinge 135, which can cause the angle between adjacent sections 137 of the connector 134 to decrease, which can shorten the length of the connector 134 (and of the insert 130) to allow the frangible container 120 to move in the housing 102, for example, along the longitudinal direction $D_1$ of the housing 102. The frangible container 120 can then be forced into contact with the projections 158 of the insert 130 to fracture the frangible container 120. Fracturing the frangible container 120 can change the frangible container 120 from its closed state to its open state and release the liquid 122 into the reservoir 103, and into fluid communication with the spore reservoir 136 and the spores 115. The liquid 122 can either include nutrient medium (e.g., germination medium) for the spores, or the liquid 122 can contact nutrient medium in a dry form (e.g., in a powdered or tablet form) to form nutrient medium, such that a mixture including the sterilized spores and nutrient medium is formed. The mixture can then be incubated prior to or during an assaying process, and the biological sterilization indicator 100 can be interrogated for signs of spore growth.

To detect a detectable change in the spores 115, the biological sterilization indicator 100 can be assayed immediately after the liquid 122 and the spores have been combined to achieve a baseline reading. After that, any detectable change from the baseline reading can be detected. The biological sterilization indicator 100 can be monitored and measured continuously or intermittently. In some embodiments, a portion of, or the entire, incubating step may be carried out prior to measuring the detectable change. In some embodiments, incubation can be carried out at one temperature (e.g., at 37° C., at 50-60° C., etc.), and measuring of the detectable change can be carried out at a different temperature (e.g., at room temperature, 25° C., or at 37° C.).

The readout time from the biological sterilization indicator 100 (i.e., the time to determine the effectiveness of the sterilization process) can be, in some embodiments, less than 8 hours, in some embodiments, less than 1 hour, in some embodiments, less than 30 minutes, in some embodiments, less than 15 minutes, in some embodiments, less than 5 minutes, and in some embodiments, less than 1 minute.

Figure 6:
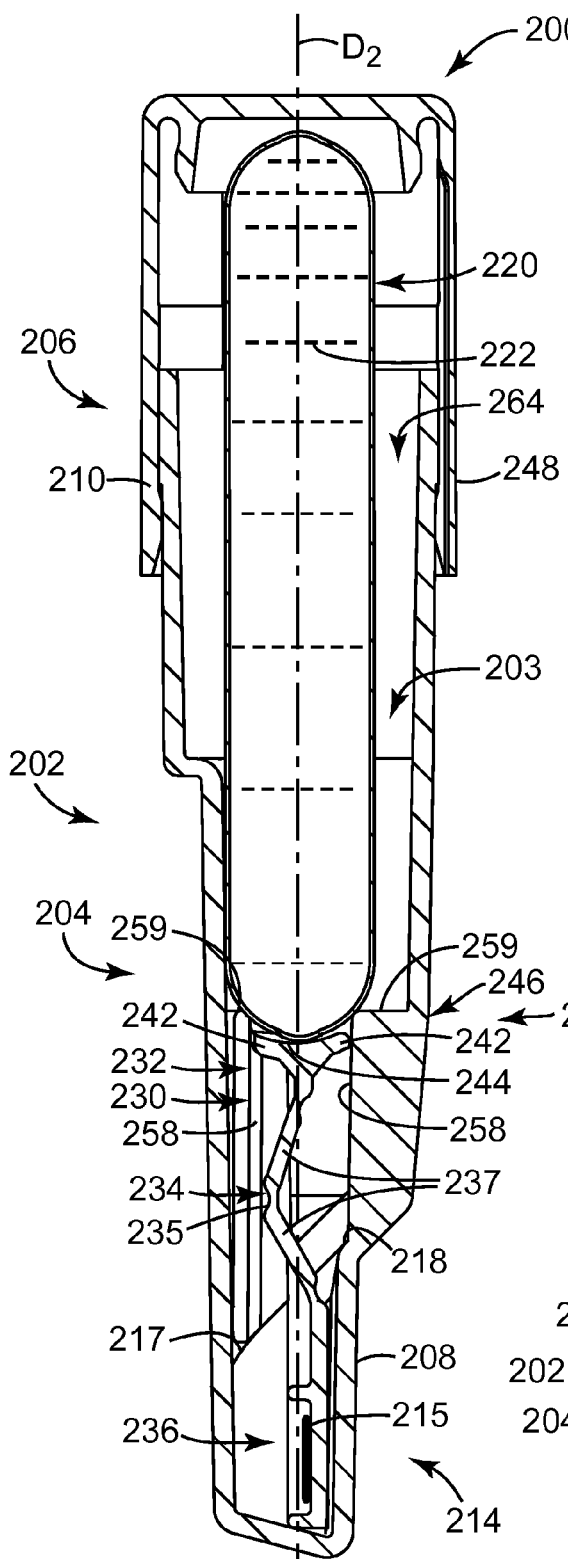
FIG. 6 is a side cross-sectional view of a biological sterilization indicator according to another embodiment of the present disclosure.
Figure 7:
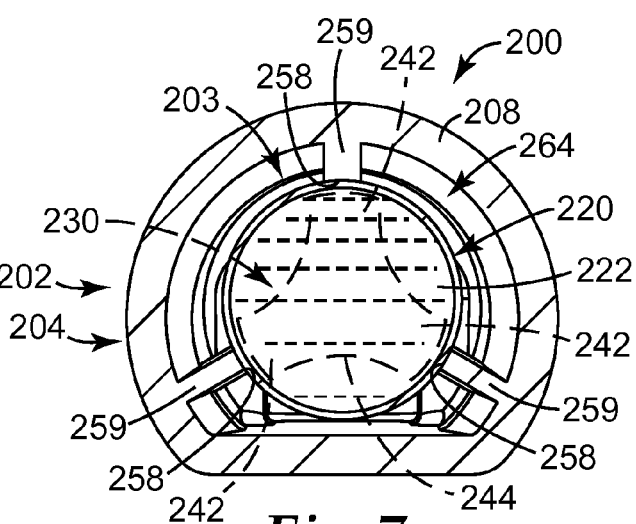
FIG. 7 is a top cross-sectional view of the biological sterilization indicator of FIG. 6.

FIGS. 6-7 illustrate a biological sterilization indicator 200 according to another embodiment of the present disclosure. The biological sterilization indicator 200 includes many of the same elements and features described above with reference to the biological sterilization indicator 100 of FIGS. 1-5, except that the biological sterilization indicator 200 includes different means for fracturing a frangible container 220. Accordingly, elements and features corresponding to elements and features in the illustrated embodiment of FIGS. 1-5 are provided with the same reference numerals in the 200 series. Reference is made to the description above accompanying FIGS. 1-5 for a more complete description of the features and elements (and alternatives to such features and elements) of the embodiment illustrated in FIGS. 6-7.

The biological sterilization indicator 200 can include a housing 202, which can include a first portion 204 and a second portion 206 (e.g., a cap) adapted to be coupled together to provide a self-contained biological sterilization indicator. The first portion 204 can include a lower portion 214 and an upper portion 216 separated by a wall 218, in which can be formed an opening 217 that provides fluid communication between the lower portion 214 and the upper portion 216. The housing 202 can include a reservoir 203 that can be defined by one or both of the first portion 204 and the second portion 206 of the housing 202. The biological sterilization indicator 200 can further include spores 215 or a locus of spores (e.g., in a spore reservoir 236) positioned in fluid communication with the reservoir 203. The housing 202 can be defined by at least one liquid impermeable wall, such as a wall 208 of the first portion 204 and/or a wall 210 of the second portion 206.

As mentioned above, the biological sterilization indicator 200 can further include the frangible container 220 that contains a liquid 222. In some embodiments, only a portion of the container 220 is frangible, for example, the container 220 can include a frangible cover (e.g., a frangible barrier, film, membrane, or the like). FIG. 7 shows a top cross-sectional view of the biological sterilization indicator 200 taken at a location near the bottom of the container 220.

As shown in FIGS. 6-7, the biological sterilization indicator 200 can further include an insert 230. In some embodiments, the insert 230 can be adapted to hold or carry the container 220, such that the container 220 is held intact in a location separate from the spores 215 during sterilization. That is, in some embodiments, the insert 230 can include (or function as) a carrier 232 for the container 220, particularly, before the container 220 is broken during the activation step (i.e., the step in which the liquid 222 is released from the container 220 and introduced to the spores 215, which typically occurs after a sterilization process).

In addition, the insert 230 can be adapted to hold the container 220 intact a position in the housing 202 that maintains at least a minimal spacing (e.g., a minimal cross-sectional area of space) between the container 220 and the housing 202 and/or between the container 220 and any other components or structures in the housing 202 (e.g., at least a portion of the insert 230, such as the carrier 232, etc.), for example, to maintain a substantially constant sterilant path 264 in the biological sterilization indicator 200. In some embodiments, the insert 230 can be adapted to hold the container 220 in a substantially consistent location in the housing 202.

In some embodiments, the insert 230 can be further adapted to allow the container 220 to move in the housing 202, e.g., longitudinally with respect to the housing 202. Such movement can be provided by a flexible connector 234 that includes a living hinge or fold 235 and adjacent sections 237. The connector 234 can function similarly as the connector 134 of FIGS. 1-5.

In some embodiments, as shown in FIG. 6, the insert 230 can be further adapted to house the spores 215. For example, in some embodiments, the insert 230 can include the spore reservoir 236, in which the spores 215 can be positioned, either directly or on a substrate. In embodiments employing a nutrient medium that is positioned to be mixed with the liquid 222 when it is released from the container 220, the nutrient medium can be positioned near or in the spore reservoir 236, and the nutrient medium can be mixed with (e.g., dissolved in) the water when the water is released from the container 220.

As shown in FIG. 6, during sterilization and before activation, the second portion 206 can be in a first position 248 with respect to the first portion 204. In the first position 248, the container 220 can be held intact in a position separate from the lower portion 214 or the spore reservoir 236, and the liquid 222 can be contained within the container 220.

After sterilization, the biological sterilization indicator 200 can be activated to release the liquid 222 from the container 220 to move the liquid 222 to the spores 215. That is, the second portion 206 of the housing 202 can be moved to a second position (e.g., see position 150 shown in FIG. 3 and described above) with respect to the first portion 204.

The insert 230 will now be described in greater detail, with particular reference to FIG. 6. As shown in FIG. 6 and mentioned above, in some embodiments, the insert 230 can include a carrier 232. In the embodiment illustrated in FIGS. 6-7, the carrier 232 includes three arms 242 and a base 244 similar to those of the embodiment illustrated in FIGS. 1-5 and described above. However, in the embodiment illustrated in FIGS. 6-7, the biological sterilization indicator 200 includes three arms 242 that are shorter than the arms 142 illustrated in FIGS. 1-5 and which do not extend around an end of the container 220 as far as the arms 142 described above and shown in FIGS. 1-5 do. In addition, as shown in FIGS. 6-7, the arms 242 do not include any projections positioned to fracture the container 220. Rather, the housing 202 includes three projections or ribs 258 that extend inwardly from the wall 208, and which are positioned to fracture the container 220 as the container 220 is moved (e.g., longitudinally downwardly) in the housing 202 as the second portion 206 is moved with respect to the first portion 204.

In some embodiments, the carrier 232 need not include the arms 242, but rather can include only the base 244. In such embodiments, the base 244 may need to be smaller than an end of the container 220, in order to provide adequate space around the container 220 for a sterilant to reach the spores 215 during sterilization.

As shown in FIGS. 6 and 7, however, the arms 242 provide support to the container 220 before activation while also providing adequate space between adjacent arms 242 for a substantially constant sterilant path 264 in the housing 202. One potential advantage that the carrier 232 may have over the carrier 132 of FIGS. 1-5 is that the carrier 232 may provide additional space around the container 220 for sterilant to move toward the spores 215 during sterilization.

In addition, in the embodiment illustrated in FIGS. 6-7, the insert 230 includes three arms 242 that are equally spaced circumferentially about the container 220. However, this need not be the case. In some embodiments, one arm 242, or the base 244 alone, is sufficient to hold the container 220 before activation. As shown in FIGS. 6 and 7, whether the carrier 232 includes arms 242, the carrier 232 can be configured to hold the container 220 in the housing 202 in a substantially consistent location to provide a substantially constant sterilant path 264 during sterilization.

In some embodiments, the projections 258 can include one or more edges (e.g., tapered edges) or points or otherwise be configured to concentrate the crushing force to increase the pressure on the container 220 in the regions adjacent the projections 258, and to facilitate fracturing the container 220 more easily and in one or more desired regions. In some embodiments, the projections 258 (e.g., an upper end 259 of the projections 258) can also function at least partially to hold a portion of the container 220, and the projections 258 can reduce the total effort or force needed to move the second portion 206 with respect to the first portion 204 and to fracture the container 220 (or a portion thereof). As shown in FIG. 6, in some embodiments, the projections 258 can be positioned to fracture the container 220 at its radiused end, for example, when an oblong or capsule-shaped container 220 is employed.

As shown in FIGS. 6 and 7, the projections 258 are integrally formed with the wall 208 of the housing 202. However, it should be understood that this need not be the case. The projections 258 can be separately formed from the housing 202 and coupled to the housing 202, or the projections 258 can be provided by an additional insert. In such embodiments, the projections 258 can each be a separate insert, or multiple projections 258 can be provided by one or more inserts. In addition, such inserts can be configured to abut the wall 218 to inhibit movement of such an insert into the proximity of the spores 215 (e.g., the lower portion 214 of the housing 202).

In addition, in some embodiments, as shown in FIG. 6, the projections 258 can extend a distance in the housing 202 along the longitudinal direction $D_2$, and the length of the projections 258 can be tailored to control the fracturing of the container 220 at a desired position in the housing 202 and in a desired manner. The configuration of the projections 258 is shown in FIGS. 6 and 7 by way of example only.

Furthermore, the biological sterilization indicator 200 is shown in FIGS. 6 and 7 as including three projections 258 by way of example only, but it should be understood that as few as one and as many as structurally necessary or possible can be employed. In addition, the biological sterilization indicator 200 is shown has having a line of symmetry, where one projection 258 (the upper projection 258 when viewed in FIG. 7) is wider and shorter than the other identical projections 258. However, it should be understood that the projections 258 can be shaped and dimensioned as desired, depending on the shape and dimensions of the housing 202, and on the manner and position desired for fracturing the container 220.

In some embodiments, as shown in FIG. 6, at least a portion of the housing 202 can include a tapered portion 246 in which the housing 202 (e.g., the wall 208) generally tapers in the longitudinal direction $D_2$ of the housing 202. As a result, the cross-sectional area in the housing 202 can generally decrease along the longitudinal direction $D_2$. In some embodiments, the projections 258 alone can vary in thickness (i.e., toward the container 220, e.g., in a radial direction) along the longitudinal direction $D_2$, such that the cross-sectional area available to the container 220 generally decreases as the container 220 is moved in the housing 202 during activation, even though the outer dimension of the housing 202 may not change.

In some embodiments, the arms 242 of the insert 230 can be movable inwardly/outwardly (e.g., radially inwardly/outwardly) with respect to the outer surface of the container 220. Such flexibility in the arms 242 can facilitate squeezing or crushing the container 220, for example, in combination with the projections 258.

In some embodiments, as shown in FIG. 2, the insert 230 can be sized and shaped to allow the container 220 to be held above the projections 258 and out of the tapered portion 246 of the housing 202 (or out of the narrower region between the projections 258) during sterilization and before activation to inhibit accidental or premature activation of the biological sterilization indicator 200. Such a configuration can also inhibit inadvertent breakage due to shock or material expansion (e.g., due to exposure to heat during a sterilization process). During activation, however, the carrier 232 can be moved (e.g., longitudinally) with respect to the projections 258 (and the housing 202), for example, in a direction toward the spore reservoir 236.

As shown in FIG. 6, the carrier 232 is configured to hold a bottom portion of the container 220, and the projections 258 are positioned to fracture the container 220 at a location near the bottom of the container 220 as its positioned in the housing 202. Such a configuration can allow the container 220 to be broken near its bottom and can facilitate removal of the liquid 222 from the container 220, which can enhance the availability of the liquid 222 to the spores 215, and can enhance the reliability of releasing the liquid 222 into fluid communication with the spores 215 (e.g., with the spore reservoir 236). Such a configuration is shown by way of example only, however, and it should be understood that the projections 258 can be configured and positioned to fracture the container 220 in any desired manner.

By way of example only, the insert 230 illustrated in FIGS. 6-7 is shown as being a unitary device that includes at least the following: means for holding the container 220 before activation; for allowing movement of the container 220 in the housing 202; for providing a substantially constant sterilant path 264; for providing a spore reservoir 236; for collecting and/or retaining portions of the fractured container 220 after activation (or at least partially inhibiting movement of portions of the fractured container 220 into the lower portion 214 of the housing 202); and/or for minimizing diffusion of the spores 215 and/or signals from the lower portion 214 to the upper portion 216 of the housing 202 after activation. However, it should be understood that in some embodiments, the insert 230 can include multiple portions that may not be part of a single, unitary device, and each of the portions can be adapted to do one or more of the above functions.

In use, the biological sterilization indicator 200 can be placed along with a sterilizing batch for a sterilization process. During sterilization, the sterilant path 264 is in fluid communication with the reservoir 203, the spore reservoir 236, and the spores 215, such that sterilant can reach the spores to produce sterilized spores. In addition, during sterilization, the frangible container 220 is in a closed state in which the liquid 222 is protected from the sterilant and is not in fluid communication with the reservoir 203, the spore reservoir 236, the spores 215, or the sterilant path 264.

Following sterilization, the effectiveness of the sterilization process can be determined using the biological sterilization indicator 200. The second portion 206 of the housing 202 can be unlocked, if previously locked in the first position 248, and moved from the first position 248 to a second position. Such movement of the second portion 206 can cause the connector 234 of the insert 230 to flex at the hinge 235, which can cause the angle between adjacent sections 237 of the connector 234 to decrease, which can shorten the length of the connector 234 (and of the insert 230) to allow the frangible container 220 to move in the housing 202, for example, along the longitudinal direction $D_2$ of the housing 202. The frangible container 220 can then be forced into contact with the projections 258 to fracture the frangible container 220. Fracturing the frangible container 220 can change the frangible container 220 from its closed state to its open state and release the liquid 222 into the reservoir 203, and into fluid communication with the spore reservoir 236 and the spores 215. The liquid 222 can either include nutrient medium (e.g., germination medium) for the spores, or the liquid 222 can contact nutrient medium in a dry form (e.g., in a powdered or tablet form) to form nutrient medium, such that a mixture including the sterilized spores and nutrient medium is formed. The mixture can then be incubated prior to or during an assaying process, and the biological sterilization indicator 200 can be interrogated for signs of spore growth.

FIGS. 8-9 illustrate a biological sterilization indicator 300 according to another embodiment of the present disclosure. The biological sterilization indicator 300 includes many of the same elements and features described above with reference to the biological sterilization indicators 100 and 200 of FIGS. 1-5 and 6-7, respectively. Accordingly, elements and features corresponding to elements and features in the illustrated embodiment of FIGS. 1-7 are provided with the same reference numerals in the 300 series. Reference is made to the description above accompanying FIGS. 1-7 for a more complete description of the features and elements (and alternatives to such features and elements) of the embodiment illustrated in FIGS. 8-9.

The biological sterilization indicator 300 can include a housing 302, which can include a first portion 304 and a second portion 306 (e.g., a cap) adapted to be coupled together to provide a self-contained biological sterilization indicator. The first portion 304 can include a lower portion 314 and an upper portion 316 separated by a wall 318, in which can be formed an opening 317 that provides fluid communication between the lower portion 314 and the upper portion 316. The housing 302 can include a reservoir 303 that can be defined by one or both of the first portion 304 and the second portion 306 of the housing 302. The biological sterilization indicator 300 can further include spores 315 or a locus of spores positioned in fluid communication with the reservoir 303 (e.g., in a spore reservoir 336). The housing 302 can be defined by at least one liquid impermeable wall, such as a wall 308 of the first portion 304 and/or a wall 310 of the second portion 306.

As mentioned above, the biological sterilization indicator 300 can further include the frangible container 320 that contains a liquid 322. In some embodiments, only a portion of the container 320 is frangible, for example, the container 320 can include a frangible cover (e.g., a frangible barrier, film, membrane, or the like). FIG. 9 shows a top cross-sectional view of the biological sterilization indicator, with the frangible container 320 removed for clarity.

As shown in FIGS. 8-9, the biological sterilization indicator 300 can further include an insert 330. By way of example only, the insert 330 includes a first portion 331, a second portion 339, and a third portion 333. However, it should be understood that two or more of the first, second and third portions 331, 339 and 333 of the insert 330 can instead be integrally formed and provided as a unitary insert 330. Alternatively, the insert 330 can include the same structures and perform the same functions as described below but broken into separate portions in a different way. In some embodiments, at least some of the features of the insert 330 can be provided by the housing 302 itself As shown in FIG. 8, during sterilization and before activation, the second portion 306 can be in a first position 348 with respect to the first portion 304. In the first position 348, the container 320 can be held intact in a position separate from the lower portion 314 or the spore reservoir 336, and the liquid 322 can be contained within the container 320.

After sterilization, the biological sterilization indicator 300 can be activated to release the liquid 322 from the container 320 to move the liquid 322 to the spores 315. That is, the second portion 306 of the housing 302 can be moved to a second position (e.g., see position 150 shown in FIG. 3 and described above) with respect to the first portion 304.

The first portion 331 of the insert 330 can be adapted to hold or carry the container 320, such that the container 320 is held intact in a location separate from the spores 315 during sterilization. That is, in some embodiments, the first portion 331 of the insert 330 can include (or function as) a carrier 332 for the container 320, particularly, before the container 320 is broken during the activation step (i.e., the step in which the liquid 322 is released from the container 320 and introduced to the spores 315, which typically occurs after a sterilization process).

In addition, the insert 330 can be adapted to hold the container 320 intact a position in the housing 302 that maintains at least a minimal spacing (e.g., a minimal cross-sectional area of space) between the container 320 and the housing 302 and/or between the container 320 and any other components or structures in the housing 302 (e.g., at least a portion of the insert 330, such as the carrier 332, etc.), for example, to maintain a substantially constant sterilant path 364 in the biological sterilization indicator 300. In some embodiments, the insert 330 can be adapted to hold the container 320 in a substantially consistent location in the housing 302.

Figure 8:
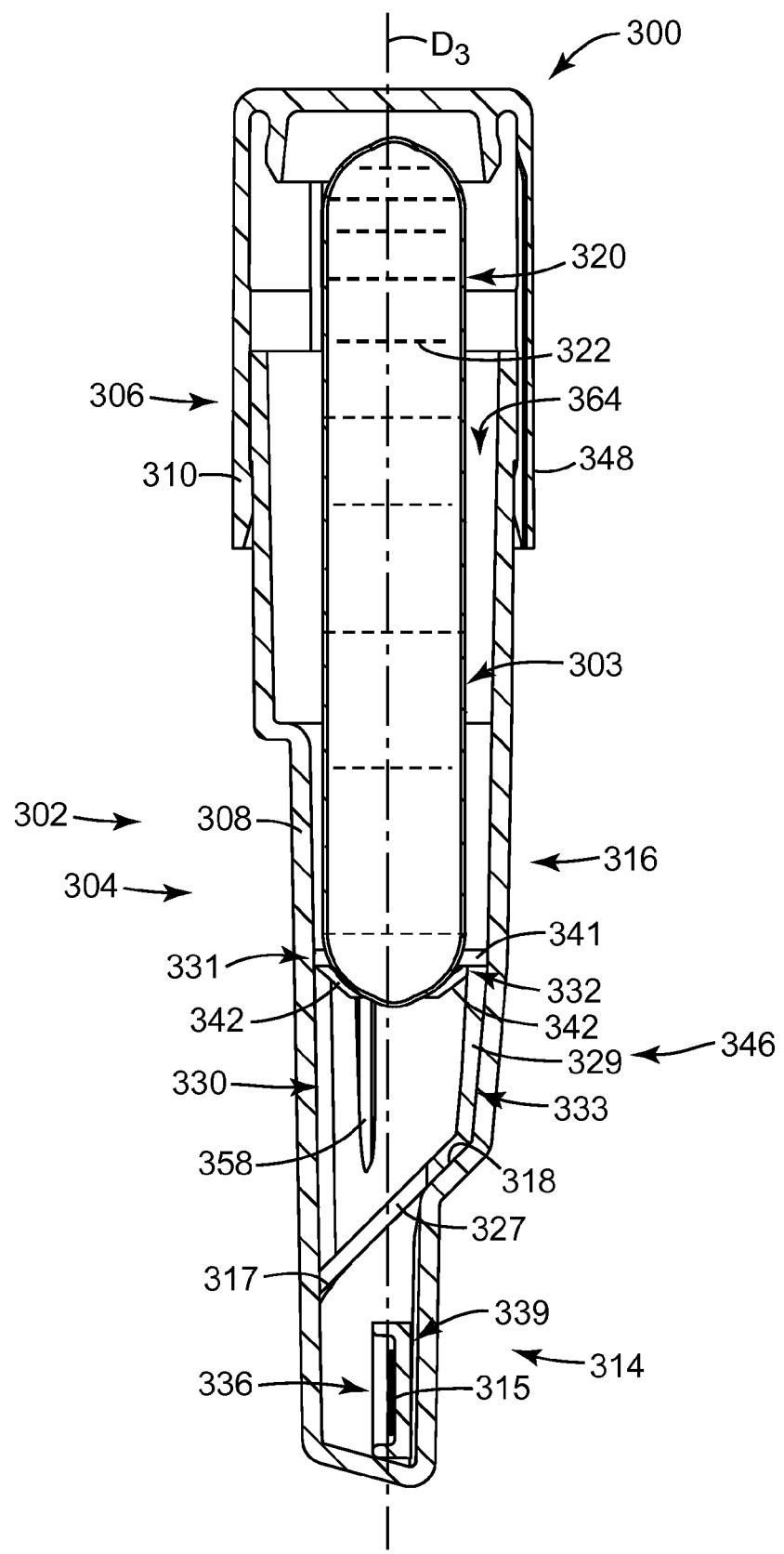
FIG. 8 is a side cross-sectional view of a biological sterilization indicator according to another embodiment of the present disclosure.
Figure 9:
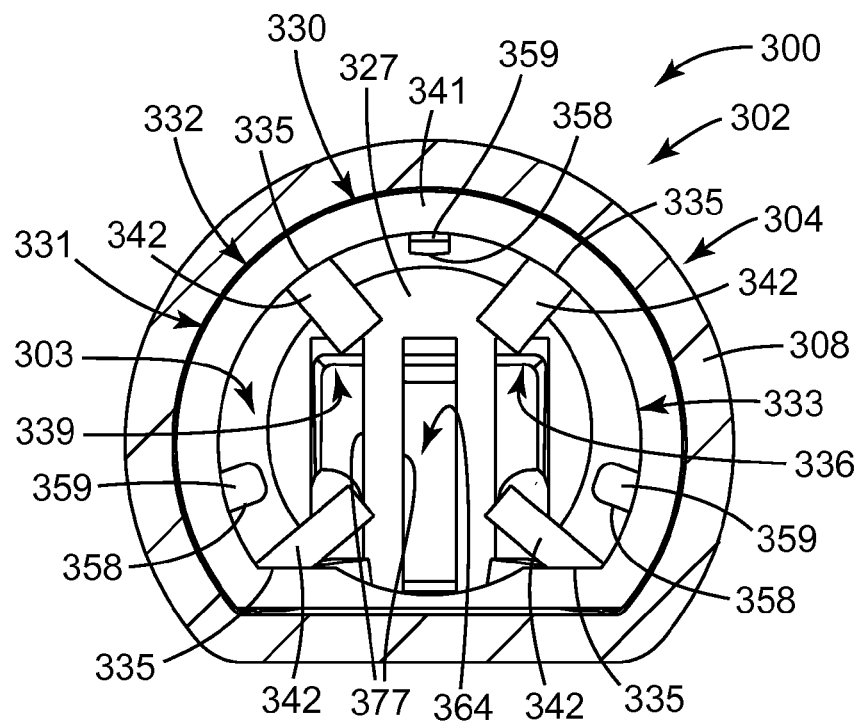
FIG. 9 is a top cross-sectional view of the biological sterilization indicator of FIG. 8, with portions removed for clarity.

In some embodiments, at least a portion of the insert 330 can be adapted to allow the container 320 to move in the housing 302, e.g., longitudinally with respect to the housing 302. In some embodiments, as shown in FIG. 8, such movement can also be provided by the first portion 331 of the insert 330. By way of example only, the first portion 331 can include one or more arms 342 (four arms 342 spaced about the inside of the wall 308 of the housing 302 are shown by way of example only) adapted to hold and support the container 320 before activation and to allow the container 320 to move in the housing 302 during activation, for example, when the second portion 306 is moved with respect to the first portion 304 of the housing 302. By way of example only, the arms 342 are shown in FIGS. 8 and 9 as being coupled to a support 341 adapted to be coupled to an upper end of the third portion 333 of the insert 330. For example, the support 341 can be dimensioned to be received in the reservoir 103 and dimensioned to sit atop or otherwise cooperate with or be coupled to the third portion 333 of the insert 330. In some embodiments, however, the biological sterilization indicator 300 does not include the support 341, and the arms 342 can be coupled to or form a portion of the third portion 333 of the insert 330 (and, in such embodiments, the insert 330 may not include a separate first portion 331), or the arms 342 can be provided by the housing 302.

The arms 342 can be formed of a variety of materials and shaped and configured in a variety of ways. In some embodiments, the arms 342 can be formed of a flexible material that can support the weight of the container 320 before activation and which can deform, distort or otherwise flex in response to movement of the second portion 306 of the housing 302. In some embodiments, as shown in FIGS. 8 and 9, the arms 342 can be integrally formed with or coupled to the support 341 at least partially by a flexible connector 334 (which can form at least a portion of the respective arm 342 or be coupled to the arm 342). Each flexible connector 334 can include one or more hinges or folds 335 (e.g., a living hinge) that allow the arm 342 to move with respect to the support 341, the third portion 333 of the insert 330 and/or the housing 302 to allow the container 320 to move in the housing 302. Other possible structures and/or materials can be employed in the arms 342 to allow the container 320 to move in the housing 302 without departing from the spirit and scope of the present disclosure.

In some embodiments, the carrier 332 need not include the arms 342, but rather can include a "trap door", or other movable or deformable/frangible barrier, film, door, or the like that supports the container 320 while also allowing sterilant to reach the spores 315 during sterilization. As shown in FIGS. 8 and 9, however, the arms 342 provide support to the container 320 before activation while also providing adequate space around the container 320 for a sterilant to move past the container 320 and to the spores 315. One potential advantage that the carrier 332 may have over barrier or trap-door type embodiments is that the arms 342 of the carrier 332 may provide additional space around the container 320 for sterilant to move toward the spores 315 during sterilization. In addition, one potential advantage that the carrier 332 may provide over barrier type embodiments or possibly over the carriers 132 and 232 described above and illustrated in FIGS. 1-5 and 6-7, respectively, is that with the carrier 332, the bottom of the container 320 can be unrestricted when the container 320 is fractured, such that the liquid 322 can be released from the container 320 and moved toward the spores 315 with relative ease and reliability.

In addition, in the embodiment illustrated in FIGS. 8-9, the first portion 331 of the insert 330 includes four arms 342 that are spaced circumferentially about the container 320. However, this need not be the case. In some embodiments, one arm 342 or a base (e.g., door, flap, film, barrier, etc.) alone, is sufficient to hold the container 320 before activation. As shown in FIGS. 8 and 9, whether the carrier 332 includes arms 342, the carrier 332 can be configured to hold the container 320 in the housing 302 separate from the spores 315.

In some embodiments, at least a portion of the insert 330 can be adapted to fracture the container 320, for example, as the container 320 is moved in the housing 302, e.g., longitudinally with respect to the housing 302. As shown in FIGS. 8-9, the arms 342 do not include any projections positioned to fracture the container 320 themselves; however, such an embodiment can be employed without departing from the spirit and scope of the present disclosure. Rather, in the embodiment illustrated in FIGS. 8 and 9, such fracturing can be provided by the third portion 333 of the insert 330. As shown in FIGS. 8 and 9, in some embodiments, the third portion 333 of the insert 330 can be positioned within the housing 302. In some embodiments, the third portion 333 can be integrally formed with the housing 302 (e.g., provided by the housing 302).

As shown in FIGS. 8-9, the third portion 333 can include a base 327, at least one sidewall 329 that can be adapted to fit within (e.g., adjacent) the wall 308 of the housing 302, and one or more projections 358 that extend inwardly from the sidewall 329. The base 327 of the third portion 333 of the insert 330 can be adapted to abut the separating wall 318 to provide the necessary resistance and force to fracture the container 320.

The projections 358 can be positioned to fracture the container 320 as the container 320 is moved with respect to the housing 302 (e.g., along a longitudinal direction $D_3$ of the housing 302). Such movement of the container 320, for example, can be in response to the second portion 306 of the housing 302 being moved with respect to the first portion 304 of the housing 302 (e.g., from the first position 348 to a second position).

In some embodiments, the projections 358 can include one or more edges (e.g., tapered edges) or points or otherwise be configured to concentrate the crushing force to increase the pressure on the container 320 in the regions adjacent the projections 358, and to facilitate fracturing the container 320 more easily and in one or more desired regions. In some embodiments, the projections 358 (e.g., an upper end 359 of the projections 358) can function at least partially to hold a portion of the container 320, and the projections 358 can reduce the total effort or force needed to move the second portion 306 with respect to the first portion 304 and to fracture the container 320 (or a portion thereof). As shown in FIG. 8, in some embodiments, the projections 358 can be positioned to fracture the container 320 at its radiused end, for example, when an oblong or capsule-shaped container 320 is employed.

As shown in FIGS. 8-9, the projections 358 are integrally formed with the sidewall 329 of the third portion 333 of the insert 330; however, it should be understood that the projections 358 can instead be integrally formed with the wall 308 of the housing 302 (e.g., similar to the projections 258 illustrated in FIGS. 6-7 and described above). In addition, in some embodiments, the projections 358 can be separately formed from the housing 302 and/or the insert 330 and coupled to the housing 302 and/or the insert 330, or the projections 358 can be provided by yet an additional insert. In such embodiments, the projections 358 can each be a separate insert, or multiple projections 358 can be provided by one or more inserts. In addition, such inserts can be configured to abut the wall 318 to inhibit movement of such an insert into the proximity of the spores 315 (e.g., the lower portion 314 of the housing 302).

In addition, in some embodiments, as shown in FIG. 8, the projections 358 can extend a distance along the longitudinal direction $D_3$, and the length and/or thickness (e.g., which can vary along the length) of the projections 358 can be tailored to control the fracturing of the container 320 at a desired position in the housing 302 and in a desired manner. The configuration of the projections 358 is shown in FIGS. 8-9 by way of example only.

Furthermore, the biological sterilization indicator 300 is shown in FIGS. 8-9 as including three projections 358 by way of example only, but it should understood that one projection 358 or as many as structurally possible can be employed. In addition, the projections 358 can be shaped and dimensioned as desired, depending on the shape and dimensions of the housing 302, on the shape and dimensions of the insert 330 or the third portion 333 of the insert 330, and/or on the manner and position desired for fracturing the container 320.

In some embodiments, as shown in FIG. 8, at least a portion of the housing 302 can include a tapered portion 346 in which the housing 302 (e.g., the wall 308, or an inner surface thereof) generally tapers in the longitudinal direction $D_3$ of the housing 302. As a result, the cross-sectional area in the housing 302 can generally decrease along the longitudinal direction $D_3$. In some embodiments, the projections 358 themselves can vary in thickness (i.e., toward the container 320, e.g., in a radial direction) along the longitudinal direction $D_3$, such that the cross-sectional area available to the container 320 generally decreases as the container 320 is moved in the housing 302 during activation, even though the outer dimension of the housing 302 may not change.

In some embodiments, as shown in FIG. 8, the insert 330 (e.g., the first portion 331 of the insert 330) can be sized and shaped to allow the container 320 to be held above the projections 358 and out of the tapered portion 346 of the housing 302 during sterilization and before activation to inhibit accidental or premature activation of the biological sterilization indicator 300. Such a configuration can also inhibit inadvertent breakage due to shock or material expansion (e.g., due to exposure to heat during a sterilization process).

As shown in FIG. 8, the carrier 332 is configured to hold a bottom portion of the container 320, and the projections 358 are positioned to fracture the container 320 at a location near the bottom of the container 320 as its positioned in the housing 302. Such a configuration can allow the container 320 to be broken near its bottom and can facilitate removal of the liquid 322 from the container 320, which can enhance the availability of the liquid 322 to the spores 315, and can enhance the reliability of releasing the liquid 322 into fluid communication with the spores 315 (e.g., with the spore reservoir 336). Such a configuration is shown by way of example only, however, and it should be understood that the projections 358 can be configured and positioned to fracture the container 320 in any desired manner.

The third portion 333 of the insert 330 can be further adapted for one or more of facilitating or allowing fluid movement (e.g., movement of the liquid 322) into the lower portion 314 of the housing 302; minimizing movement of fractions or portions (e.g., solids) of the fractured container 320 into the lower portion 314 of the housing 302, that is, collecting and/or retaining portions of the fractured container 320; and/or minimizing diffusion of spores 315 and/or signals out of the lower portion 314 of the housing 302. For example, in some embodiments, as shown in FIGS. 8-9, the third portion 333 of the insert 330 can be shaped and dimensioned to abut or be coupled to the wall or partition 318. That is, in some embodiments, the base 327 can be dimensioned to fit within the upper portion 314 of the housing 302 and abut the wall 318. In addition, the base 327 can include one or more apertures 377 that can function as a grate to allow the liquid 322 to move into the lower portion 314 of the housing 302 when the liquid 322 is released from the container 320, while inhibiting the movement of portions of the fractured container 320 from moving into the proximity of the spores 315, where such portions may affect detection (e.g., optical detection) of spore growth. In addition, the base 327 and/or the one or more apertures 377 can be configured to inhibit fluid from moving upwardly in the housing 302, i.e., from the lower portion 314 to the upper portion 316 of the housing 302.

By way of example only, the base 327 illustrated in FIGS. 8 and 9 includes three rectilinear apertures 377; however, it should be understood that fewer or more apertures 377 can be employed, and the apertures and base 327 can include a variety of shapes and configurations to facilitate fluid movement into the lower portion 314, while collecting and/or retaining portions of the fractured container 320, and while potentially inhibiting movement of fluid out of the lower portion 314 (e.g., the apertures 377 can taper toward the spores 315, such that the apertures 377 are smaller on the spore side of the base 327).

In some embodiments, as shown in FIG. 8, the insert 330 can be further adapted to house the spores 315. For example, in the embodiment illustrated in FIGS. 8-9, the second portion 339 of the insert 330 can include the spore reservoir 336, in which the spores 315 can be positioned, either directly or on a substrate. In some embodiments, the biological sterilization indicator 300 does not include a spore reservoir 336 (or a second portion 339 of the insert 330) and the spores 315 can be positioned in the lower portion 314 of the housing 302 directly or on a substrate. The spore reservoir 336 is shown by way of example only as being substantially similar to that of the biological sterilization indicators 100 and 200 illustrated in FIGS. 1-5 and 6-7, respectively. However, it should be understood that a variety of different structures can be used to provide a spore reservoir 336.

By way of example only, the insert 330 illustrated in FIGS. 8-9 is shown as being formed of three separate portions 331, 333 and 339. Together, the three portions 331, 333 and 339 of the insert 330 include at least the following: means for holding the container 320 before activation; for allowing movement of the container 320 in the housing 302; for providing a sterilant path 364; for providing a spore reservoir 336; for collecting and/or retaining portions of the fractured container 320 after activation (or at least partially inhibiting movement of portions of the fractured container 320 into the lower portion 314 of the housing 302); and/or for minimizing diffusion of the spores 315 and/or signals from the lower portion 314 to the upper portion 316 of the housing 302 after activation. However, it should be understood that the insert 330 can be divided into portions differently or can be formed of a single unitary device, or that portions can be provided by the housing 302 itself.

In use, the biological sterilization indicator 300 can be placed along with a sterilizing batch for a sterilization process. During sterilization, the sterilant path 364 is in fluid communication with the reservoir 303, the spore reservoir 336, and the spores 315, such that sterilant can reach the spores to produce sterilized spores. In addition, during sterilization, the frangible container 320 is in a closed state in which the liquid 322 is protected from the sterilant and is not in fluid communication with the reservoir 303, the spore reservoir 336, the spores 315, or the sterilant path 364.

Following sterilization, the effectiveness of the sterilization process can be determined using the biological sterilization indicator 300. The second portion 306 of the housing 302 can be unlocked, if previously locked in the first position 348, and moved from the first position 348 to a second position. Such movement of the second portion 306 can cause the one or more arms 342 to move out of the way of the container 320 (e.g., by causing the connectors 334 of the first portion 331 of the insert 330 to flex at the respective hinges 335), which can allow the frangible container 320 to move in the housing 302, for example, along the longitudinal direction $D_3$ of the housing 302. The frangible container 320 can then be forced into contact with the projections 358 provided by the third portion 333 of the insert 330 to fracture the frangible container 320. Fracturing the frangible container 320 can change the frangible container 320 from its closed state to its open state and release the liquid 322 into the reservoir 303, and into fluid communication with the spore reservoir 336 and the spores 315. Fractured portions of the container 320 can be collected, or at least inhibited from moving into proximity of the spores 315, for example, by the third portion 333 of the insert 330. The liquid 322 can either include nutrient medium (e.g., germination medium) for the spores, or the liquid 322 can contact nutrient medium in a dry form (e.g., in a powdered or tablet form) to form nutrient medium, such that a mixture including the sterilized spores and nutrient medium is formed. The mixture can then be incubated prior to or during an assaying process, and the biological sterilization indicator 300 can be interrogated for signs of spore growth.

FIGS. 10-13 illustrate a biological sterilization indicator 400 according to another embodiment of the present disclosure. The biological sterilization indicator 400 includes many of the same elements and features described above with reference to the biological sterilization indicators 100, 200 and 300 of FIGS. 1-5, 6-7 and 8-9, respectively. Accordingly, elements and features corresponding to elements and features in the illustrated embodiment of FIGS. 1-9 are provided with the same reference numerals in the 400 series. Reference is made to the description above accompanying FIGS. 1-9 for a more complete description of the features and elements (and alternatives to such features and elements) of the embodiment illustrated in FIGS. 10-13.

The biological sterilization indicator 400 can include a housing 402, which can include a first portion 404 and a second portion 406 (e.g., a cap) adapted to be coupled together to provide a self-contained biological sterilization indicator. The first portion 404 can include a lower portion 414 and an upper portion 416 separated by a wall 418, in which can be formed an opening 417 that provides fluid communication between the lower portion 414 and the upper portion 416. The housing 402 can include a reservoir 403 that can be defined by one or both of the first portion 404 and the second portion 406 of the housing 402. The biological sterilization indicator 400 can further include spores 415 or a locus of spores positioned in fluid communication with the reservoir 403 (e.g., in a spore reservoir 436).

Figure 10:
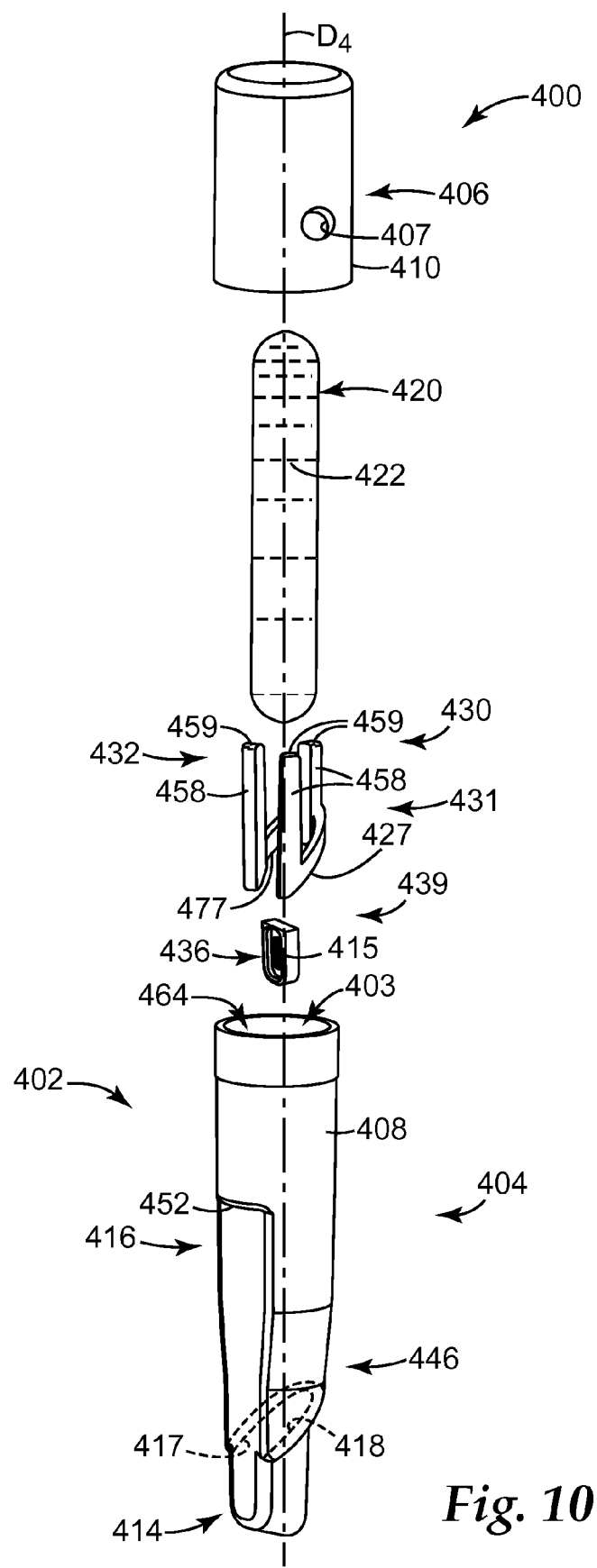
FIG. 10 is an exploded perspective view of a biological sterilization indicator according to another embodiment of the present disclosure.

The housing 402 can be defined by at least one liquid impermeable wall, such as a wall 408 of the first portion 404 and/or a wall 410 of the second portion 406. As shown in FIG. 10, the second portion 406 of the housing 402 can include one or more apertures 407 to provide fluid communication between the interior of the housing 402 (e.g., the reservoir 403) and ambience. For example, the one or more apertures 407 can provide fluid communication between the spores 415 and ambience during a sterilization process, and can serve as an inlet into the biological sterilization indicator 400 and as an inlet of a sterilant path 464.

Figure 13:
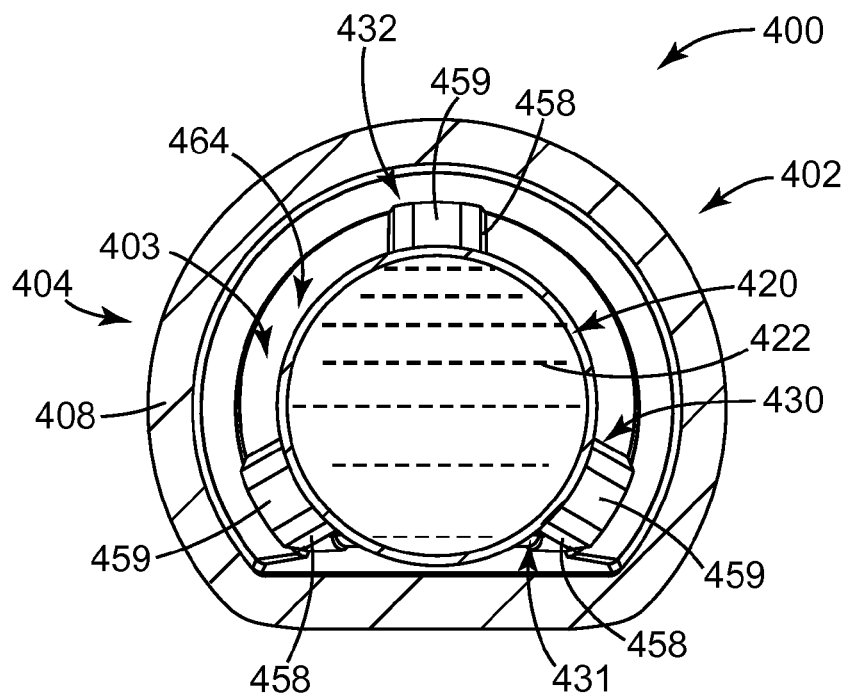
FIG. 13 is a top cross-sectional view of the biological sterilization indicator of FIGS. 10-12.

As mentioned above, the biological sterilization indicator 400 can further include the frangible container 420 that contains a liquid 422. In some embodiments, only a portion of the container 420 is frangible, for example, the container 420 can include a frangible cover (e.g., a frangible barrier, film, membrane, or the like). FIG. 13 shows a top cross-sectional view of the biological sterilization indicator 400 taken at a location near the bottom of the container 420.

As shown in FIGS. 10-13, the biological sterilization indicator 400 can further include an insert 430. By way of example only, the insert 430 includes a first portion 431 and a second portion 439. However, it should be understood that the first and second portions 431 and 439 of the insert 430 can instead be integrally formed and provided as a unitary insert 430. Alternatively, the insert 430 can include the same structures and perform the same functions as described below but broken into separate portions in a different way. In some embodiments, at least some of the features of the insert 430 can be provided by the housing 402 itself.

Figure 11:
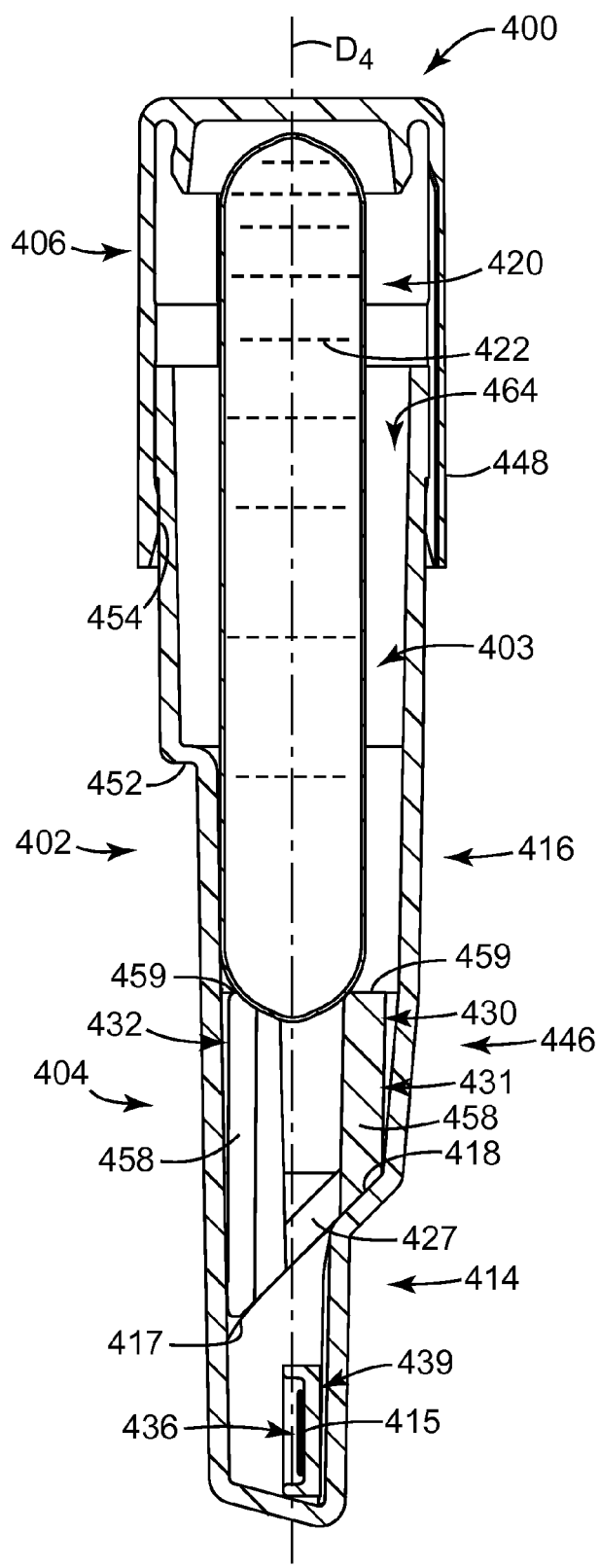
FIG. 11 is an assembled side cross-sectional view of the biological sterilization indicator of FIG. 10, before activation.
Figure 12:
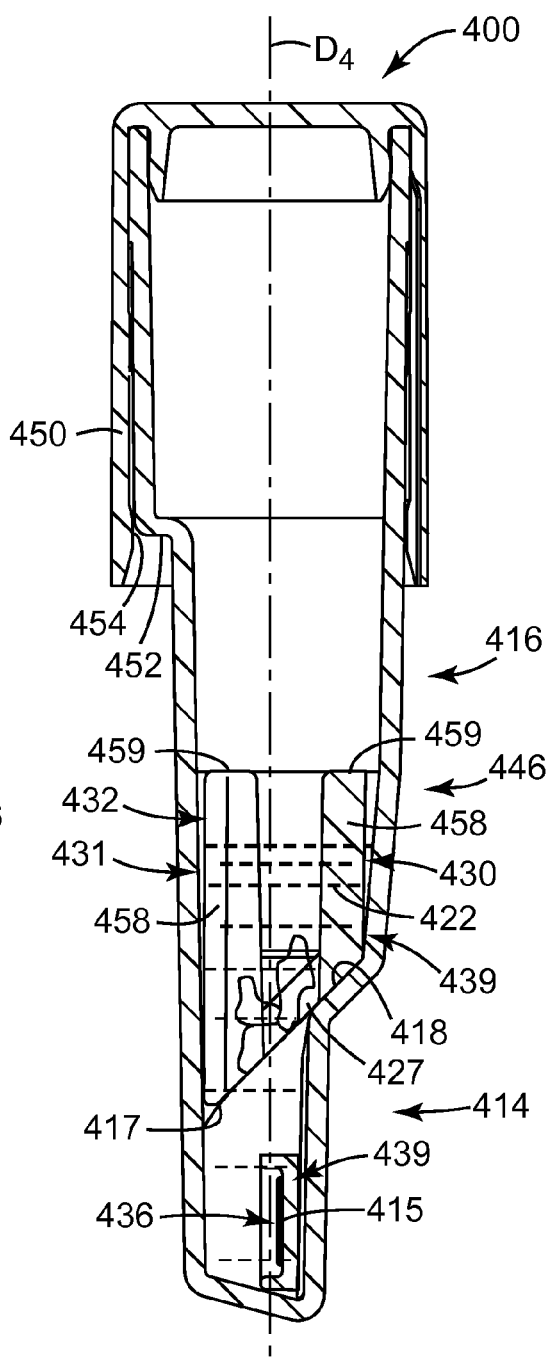
FIG. 12 is a side cross-sectional view of the biological sterilization indicator of FIGS. 10 and 11, after activation.

As shown in FIGS. 11 and 12, the second portion 406 of the housing 402 can be adapted to be coupled to the first portion 404. For example, as illustrated in FIGS. 10-12, the second portion 406 can be adapted to be coupled to the upper portion 416 of the first portion 404 of the housing 402. In some embodiments, as shown in FIGS. 10-12, the second portion 406 can be in the form of a cap that can be dimensioned to receive at least a portion of the first portion 404 of the housing 402.

As shown in FIG. 11, during sterilization and before activation, the second portion 406 can be in a first position 448 with respect to the first portion 404. In the first position 448, the container 420 can be held intact in a position separate from the lower portion 414 or the spore reservoir 436, and the liquid 422 can be contained within the container 420.

As shown in FIG. 12, after sterilization, the biological sterilization indicator 400 can be activated to release the liquid 422 from the container 420 to move the liquid 422 to the spores 415. That is, the second portion 406 of the housing 402 can be moved to a second position 450 with respect to the first portion 404. Similar to the embodiment illustrated in FIGS. 1-4 and described above, the first portion 404 of the housing 402 can include a step or overhang 452 in its outer surface, and the second portion 406 can include a lip or protrusion 454 that can be adapted to engage with the step 452 on the first portion 404 when the second portion 406 is moved from the first position 448 to the second position 450. In such embodiments, the second portion 406 can reversibly engage the first portion 404 in the second position 450, and in some embodiments, the second portion 406 can irreversibly engage the first portion 404. However, it should be understood that the structures and coupling means for the first portion 104 and the second portion 106 are shown in FIGS. 10-13 by way of example only, and any of the above-described coupling means can instead be employed between the first portion 404 and the second portion 406 of the housing 402.

The first portion 431 of the insert 430 can be adapted to hold or carry the container 420, such that the container 420 is held intact in a location separate from the spores 415 during sterilization. That is, in some embodiments, the first portion 431 of the insert 430 can include (or function as) a carrier 432 for the container 420, particularly, before the container 420 is broken during the activation step (i.e., the step in which the liquid 422 is released from the container 420 and introduced to the spores 415, which typically occurs after a sterilization process).

In addition, the insert 430 can be adapted to hold the container 420 intact a position in the housing 402 that maintains at least a minimal spacing (e.g., a minimal cross-sectional area of space) between the container 420 and the housing 402 and/or between the container 420 and any other components or structures in the housing 402 (e.g., at least a portion of the insert 430, such as the carrier 432, etc.), for example, to maintain a substantially constant sterilant path 464 in the biological sterilization indicator 400. In some embodiments, the insert 430 can be adapted to hold the container 420 in a substantially consistent location in the housing 402.

In some embodiments, at least a portion of the insert 430 can be adapted to allow the container 420 to move in the housing 402, e.g., longitudinally with respect to the housing 402. In some embodiments, as shown in FIGS. 10-12, such movement can be provided by the first portion 431 of the insert 430. By way of example only, the first portion 431 can include one or more projections 458 (three projections 458 spaced about the container 420 are shown by way of example only) adapted to hold and support the container 420 before activation and to allow the container 420 to move in the housing 402 during activation, for example, when the second portion 406 is moved with respect to the first portion 404 of the housing 402. By way of example only, the projections 458 are shown in FIGS. 10-13 as being coupled to a base or support 427 adapted to abut the separating wall 418. For example, the base 427 can be dimensioned to be received in the reservoir 403 and dimensioned to sit atop, abut, or otherwise cooperate with or be coupled to the separating wall 418. In some embodiments, however, the insert 430 does not include the base 427, and the projections 458 can be coupled to or form a portion of the housing 402. In some embodiments, the insert 430 is integrally formed with or provided by the housing 402.

By way of example only, the projections 458 are illustrated as being relatively rigid and stationary. That is, unlike the arms 142, 242 and 342 of the embodiments described above and shown in FIGS. 1-5, 6-7 and 8-9, respectively, the projections 458 may not be adapted to substantially flex, distort, deform or otherwise heed to the container 420 as it is moved in the housing 402. Rather, the projections 458 can each be configured to have an upper end 459 atop which the container 420 can be positioned and held intact before activation. As shown in FIG. 11, in some embodiments, the projections 458 can be positioned to fracture the container 420 at its radiused end, for example, when an oblong or capsule-shaped container 420 is employed.

One potential advantage of having the projections 458 form at least a portion of the carrier 432 is that the bottom of the container 420 can be unrestricted when the container 420 is fractured, such that the liquid 422 can be released from the container 420 and moved toward the spores 415 with relative ease and reliability.

While the projections 458 are illustrated as being relatively rigid and stationary in the embodiment shown in FIGS. 10-13, in some embodiments, the insert 430 can be adapted to be movable with respect to a housing of a biological sterilization indicator, for example, by virtue of a connector (such as the connector 134 shown in FIGS. 1-5 and equivalents thereof). In such embodiments, a connector can couple the first portion 431 of the insert 430 to the second portion 439 of the insert 430, or another portion of the insert 430.

Furthermore, in some embodiments, the projections 458 can be movable (e.g., can flex) toward and away from the container 420 (e.g., radially inwardly and radially outwardly with respect to the container 420), similar to the movement of the arms 142 illustrated in FIGS. 1-5 and described above. In such embodiments, another structure or the housing 402 can cause the projections 458 to move in and out. For example, in some embodiments, the projections 458 can flex in or out in response to the projections 458 (or the first portion 431 of the insert 430) being moved in the housing 402. In such embodiments, the projections 458 can include additional projections (e.g., similar to the projections 158 illustrated in FIGS. 1-5 and described above) that extend toward the container 420. In such embodiments, the insert 430 can be used to fracture the container 420 in a direction that is substantially perpendicular to a flat side of the container 420, for example, when an oblong or capsule-shaped container 420 is employed. In such embodiments, fracturing the container 420 along its side can be achieved, along with maintaining some open spaces around the lower end of the container 420 to facilitate moving the liquid 422 from the container 420 to the proximity of the spores 415 when the container 420 is fractured.

In the embodiment illustrated in FIGS. 1-5, the carrier components are referred to as "arms" 142, while the breaking components are referred to as "projections" 158. In the embodiment illustrated in FIGS. 10-13, the carrier and breaking components are referred to as "projections" 458. However, it should be understood that the terms "arms" and "projections" are used merely for clarity and descriptive purposes, but that, in some embodiments, such terms can be used interchangeably, and the arms 142 can instead be referred to as "projections" 142, the projections 158 can be referred to as "protrusions" or extensions of the projections 142, etc.

In some embodiments, at least a portion of the insert 430 can be adapted to fracture the container 420, for example, as the container 420 is moved in the housing 402, e.g., longitudinally with respect to the housing 402. As shown in FIGS. 10-13, fracturing of the container 420 can also be provided by the first portion 431 of the insert 430, and particularly, by the projections 458. As shown in FIGS. 10-12, the base 427 of the first portion 431 of the insert 430 can be adapted to abut the separating wall 418 to provide the necessary resistance and force to fracture the container 420 as the container 420 is moved in the housing 402.

The projections 458 can be positioned to fracture the container 420 as the container 420 is moved with respect to the housing 402 (e.g., along a longitudinal direction $D_4$ of the housing 402), for example, in response to the second portion 406 of the housing 402 being moved with respect to the first portion 404 of the housing 402 (e.g., from the first position 448 to the second position 450).

In some embodiments, the projections 458 can include one or more edges (e.g., tapered edges) or points or otherwise be configured to concentrate the crushing force to increase the pressure on the container 420 in the regions adjacent the projections 458, and to facilitate fracturing the container 420 more easily and in one or more desired regions. In some embodiments, such concentration of force can reduce the total effort or force needed to move the second portion 406 with respect to the first portion 404 and to fracture the container 420 (or a portion thereof).

As shown in FIGS. 10-13, the projections 458 are integrally formed with the base 427 of the first portion 431 of the insert 430; however, it should be understood that the projections 458 can instead be integrally formed with the wall 408 of the housing 402 (e.g., similar to the projections 258 illustrated in FIGS. 6-7 and described above). In addition, in some embodiments, the projections 458 can be coupled to the housing 402 and/or the second portion 439 of the insert 430, or the projections 458 and the base 427 can be provided by separate inserts 430. In such embodiments, the projections 458 can each be a separate insert, or multiple projections 458 can be provided by one or more inserts. In addition, the first portion 431 of the insert 430 can be configured to abut the wall 418 to inhibit movement of the first portion 431 of the insert 430 into the proximity of the spores 415 (e.g., the lower portion 414 of the housing 402).

In addition, in some embodiments, as shown in FIGS. 10-12, the projections 458 can extend a distance along the longitudinal direction $D_4$, and the length and/or thickness (e.g., which can vary along the length) of the projections 458 can be tailored to control the fracturing of the container 420 at a desired position in the housing 402 and in a desired manner. The configuration of the projections 458 is shown in FIGS. 8-9 by way of example only.

In general, each of the projections 458 is shown by way of example only as increasing in thickness (e.g., inwardly toward the container 420 or center of the housing 402) along the longitudinal direction $D_4$ toward the spores 415. Such a configuration can decrease the cross-sectional area that is available to the container 420, as the container 420 is moved toward the spores 415, for example, in response to the second portion 406 being moved to the second position 450.

Furthermore, the biological sterilization indicator 400 is shown in FIGS. 10-13 as including three projections 458 by way of example only, but it should understood that one projection 458 or as many as structurally possible can be employed. In addition, the projections 458 can be shaped and dimensioned as desired, depending on the shape and dimensions of the housing 402, on the shape and dimensions of the insert 430 or the first portion 431 of the insert 430, and/or on the manner and position desired for fracturing the container 420.

In some embodiments, as shown in FIGS. 10-12, at least a portion of the housing 402 can include a tapered portion 446 in which the housing 402 (e.g., the wall 408, or an inner surface thereof) generally tapers in the longitudinal direction $D_4$ of the housing 402. As a result, the cross-sectional area in the housing 402 can generally decrease along the longitudinal direction $D_4$. In some embodiments, the one or more projections 458 alone can vary in thickness (i.e., toward the container 420, e.g., in a radial direction) along the longitudinal direction $D_4$, such that the cross-sectional area available to the container 420 generally decreases as the container 420 is moved in the housing 402 during activation, even though the dimensions of the housing 402 do not change (e.g., even if the housing 402 does not include any tapered portion 446, either internally or externally).

As shown in FIGS. 10-13, the upper end 459 of each of the projections 458 includes a rounded, curved or arcuate surface, which can facilitate movement of the container 420 from the first position 448 in which the container 420 sits at least partially above the upper end 459 of the projection 458 to a position in which the container 420 is forced into the smaller cross-sectional area region in between the projections 458 (or between the wall 408 of the housing 402 and one or more projections 458). In addition, the rounded upper end 459 can inhibit premature breakage of the container 420, which can inhibit premature activation of the biological sterilization indicator 400 (i.e., premature release of the liquid 422).

In some embodiments, as shown in FIG. 11, the insert 430 (e.g., the first portion 431 of the insert 430) can be sized and shaped to allow the container 420 to be held above the projections 458 and out from the region adjacent any portion of an inwardly-facing surface of one or more of the projections 458 to inhibit accidental or premature activation of the biological sterilization indicator 400. Such a configuration can also inhibit inadvertent breakage due to shock or material expansion (e.g., due to exposure to heat during a sterilization process).

As shown in FIGS. 10-12, the carrier 432, which can be formed at least partially by the upper ends 459 of the projections 458, can be configured to hold a bottom portion of the container 420, and the projections 458 can be positioned to fracture the container 420 at a location near the bottom of the container 420 as its positioned in the housing 402. Such a configuration can allow the container 420 to be broken near its bottom and can facilitate removal of the liquid 422 from the container 420, which can enhance the availability of the liquid 422 to the spores 415, and can enhance the reliability of releasing the liquid 422 into fluid communication with the spores 415 (e.g., with the spore reservoir 436). Such a configuration is shown by way of example only, however, and it should be understood that the projections 458 can be configured and positioned to fracture the container 420 in any desired manner.

In some embodiments, the first portion 431 of the insert 430 (e.g., the base 427) can be adapted for one or more of facilitating or allowing fluid movement (e.g., movement of the liquid 422) into the lower portion 414 of the housing 402; minimizing movement of fractions or portions (e.g., solids) of the fractured container 420 into the lower portion 414 of the housing 402, that is, collecting and/or retaining portions of the fractured container 420; and/or minimizing diffusion of the spores 415 and/or signals out of the lower portion 414 of the housing 402. For example, in some embodiments, the base 427 can be configured to function as a grate, similar to the base 327 described above with respect to FIGS. 8 and 9.

In the embodiment illustrated in FIGS. 10-13, the base 427 of the first portion 431 of the insert 430 is generally U-shaped or horseshoe-shaped and includes a central aperture 477 (see FIG. 10) that facilitates the movement of sterilant toward the spores 415 during sterilization and the movement of the liquid 422 toward the spores 415 during activation. The horseshoe shape of the base 427 can increase the opening between the upper portion 416 and the lower portion 414 of the housing 402; however, this shape is shown by way of example only, and other shapes can be employed.

In the embodiment illustrated in FIGS. 10-13, the first portion 431 of the insert 430 is illustrated as including three projections 458 that are approximately equally spaced about the container 420 and/or about the inner surface of the wall 408 of the housing 402. However, in some embodiments, the first portion 431 can include one solid (e.g., substantially annular) projection 458 that extends upwardly from the base 427 along the wall 408. However, employing one or more narrower (e.g., in an angular dimension) projections 458, such as those shown in FIGS. 10-13, can provide a substantially constant or substantially unobstructed sterilant path 464 around the container 420.

In some embodiments, as shown in FIGS. 10-13, the insert 430 can be further adapted to house the spores 415. For example, in the embodiment illustrated in FIGS. 10-13, the second portion 439 of the insert 430 can include the spore reservoir 436, in which the spores 415 can be positioned, either directly or on a substrate. In some embodiments, the biological sterilization indicator 400 does not include a spore reservoir 436 (or a second portion 439 of the insert 430), and the spores 415 can be positioned in the lower portion 414 of the housing 402 directly or on a substrate. The spore reservoir 436 is shown by way of example only as being substantially similar to that of the biological sterilization indicators 100, 200 and 300 illustrated in FIGS. 1-5, 6-7 and 8-9, respectively. However, it should be understood that a variety of different structures can be used to provide a spore reservoir 436.

By way of example only, the insert 430 illustrated in FIGS. 10-13 is shown as being formed of two separate portions 431 and 439. Together, the two portions 431 and 439 of the insert 430 include at least the following: means for holding the container 420 before activation, for allowing movement of the container 420 in the housing 402, for fracturing the container 420, for facilitating movement of the liquid 422 into the lower portion 414 of the housing 402, and/or for providing a sterilant path 464. However, it should be understood that the insert 430 can be divided into portions differently or can be formed of a single unitary device, or that portions can be provided by the housing 402 itself.

In use, the biological sterilization indicator 400 can be placed along with a sterilizing batch for a sterilization process. During sterilization, the sterilant path 464 is in fluid communication with the reservoir 403, the spore reservoir 436, and the spores 415, such that sterilant can reach the spores to produce sterilized spores. In addition, during sterilization, the frangible container 420 is in a closed state in which the liquid 422 is protected from the sterilant and is not in fluid communication with the reservoir 403, the spore reservoir 436, the spores 415, or the sterilant path 464.

Following sterilization, the effectiveness of the sterilization process can be determined using the biological sterilization indicator 400. The second portion 406 of the housing 402 can be unlocked, if previously locked in the first position 448, and moved from the first position 448 (see FIG. 11) to the second position 450 (see FIG. 12). Such movement of the second portion 406 can cause the container 420 to move in the housing 402 (e.g., along the longitudinal direction $D_4$) from a position above the upper ends 459 of the projections 458 to a position within the interior of the projections 458, which can cause the frangible container 420 to fracture. Fracturing the frangible container 420 can change the frangible container 420 from its closed state to its open state and release the liquid 422 into the reservoir 403, and into fluid communication with the spore reservoir 436 and the spores 415. The liquid 422 can either include nutrient medium (e.g., germination medium) for the spores, or the liquid 422 can contact nutrient medium in a dry form (e.g., in a powdered or tablet form) to form nutrient medium, such that a mixture including the sterilized spores and nutrient medium is formed. The mixture can then be incubated prior to or during an assaying process, and the biological sterilization indicator 400 can be interrogated for signs of spore growth.

FIGS. 14-17 illustrate inserts 530, 630, 730 and 830 according to other embodiments of the present disclosure. The inserts 530, 630, 730 and 830 include many of the same elements and features described above with reference to the inserts 130, 230, 330 and 430 of FIGS. 1-5, 6-7, 8-9 and 10-13, respectively. Accordingly, elements and features corresponding to elements and features in the illustrated embodiment of FIGS. 1-13 are provided with the same reference numerals in the 500, 600, 700 or 800 series. Reference is made to the description above accompanying FIGS. 1-13 for a more complete description of the features and elements (and alternatives to such features and elements) of the embodiments illustrated in FIGS. 14-17. In addition, any of the additional disclosure or alternative embodiments mentioned below with respect to the inserts 530, 630, 730 and 830 can be equally applied to any of the biological sterilization indicators 100, 200, 300 and 400 described above and illustrated in FIGS. 1-13.

Each of the inserts 530, 630, 730 and 830 share some similarities with the third portion 333 of the insert 330 of FIGS. 8-9 and with the first portion 431 of the insert 430 of FIGS. 10-13. As a result, any of the inserts 530, 630, 730 and 830 can be used as the third portion 333 of the insert 330 of FIGS. 8-9 and/or of the first portion 431 of the insert 430 of FIGS. 10-13. However, it should be understood that any of the inserts 530, 630, 730 and 830 can be employed in any of the biological sterilization indicators 100, 200, 300 or 400 described above and illustrated in FIGS. 1-13, in lieu of or in addition to the structures shown in FIGS. 1-13 and described above.

Each of the inserts 530, 630, 730 and 830 is adapted to hold and support a frangible container before activation of a biological sterilization indicator, to allow the container to move in the housing (e.g., during activation of the biological sterilization indicator), as well as to fracture the container during activation, for example, as a second portion of a housing is moved with respect to a first portion of the housing.

Figure 14:
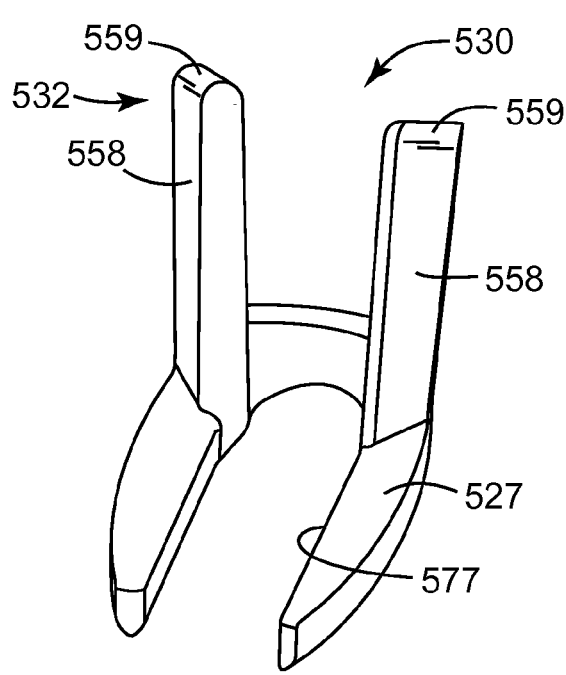
FIG. 14 is a perspective view of an insert according to another embodiment of the present disclosure.

As shown in FIG. 14, in some embodiments, the insert 530 can include one or more projections 558 adapted to hold and support a frangible container before activation and to allow the container to move in the biological sterilization indicator during activation. By way of example only, the projections 558 are shown in FIG. 14 as being coupled to a base or support 527, which can be adapted to abut a separating wall in a biological sterilization indicator (e.g., the wall 118 shown in FIGS. 1-4). For example, the base 527 is angled to cooperate with or be coupled to an angled separating wall. In addition, the base 527 (and the entire insert 530) can be dimensioned to be received within a biological sterilization indicator.

By way of example only, the projections 558 are illustrated as being relatively rigid and stationary, and the projections 558 can each be configured to have an upper end 559 atop which a container can be positioned and held intact before activation. That is, the upper ends 559 can function as a carrier 532. The insert 530, and particularly, the carrier 532, can be adapted to hold or carry a container, such that the container is held intact in a location separate from spores during sterilization. In addition, the insert 530, and particularly, the carrier 532, can be adapted to hold the container intact in a position in a biological sterilization indicator that maintains at least a minimal spacing (e.g., a minimal cross-sectional area of space) between the container and a housing or wall of the biological sterilization indicator and/or between the container and any other components or structures in the housing (e.g., at least a portion of the insert 530, such as the carrier 532, etc.), for example, to maintain a substantially constant sterilant path in the biological sterilization indicator. In some embodiments, the insert 530 can be adapted to hold the container in a substantially consistent location in the housing.

By way of example only, the insert 530 includes two projections 558. One potential advantage of having the projections 558 hold the container without requiring an additional support or base to hold the container, along with having fewer (e.g., two rather than three or more) projections 558 is that the bottom of the container can be unrestricted when the container is fractured, such that any liquid contained within the container can be released from the container and moved toward spores in a biological sterilization indicator with relative ease and reliability. In some embodiments, the projections 558 can be positioned to fracture the container at a radiused end, for example, when an oblong or capsule-shaped container is employed.

The base 527 of the insert 530 can be adapted to abut an inner wall, partition or base of a biological sterilization indicator to provide the necessary resistance and force to fracture a container as the container is moved with respect to the insert 530. In some embodiments, however, the insert 530 can be adapted to be movable with respect to a housing of a biological sterilization indicator by virtue of a connector (such as the connector 134 shown in FIGS. 1-5 and equivalents thereof).

By way of example only, the projections 558 each include an inwardly-facing surface that is substantially flat. As a result, in order to restrict a frangible container and cause it to fracture as it is moved with respect to the insert 530, the projections 558 can either vary in thickness or be angled with respect to a direction (e.g., a longitudinal direction) of a biological sterilization indicator along which the container is moved during activation. Such varying thickness or angling can create a generally decreasing cross-sectional area that is available to the container as it is moved in the biological sterilization indicator during activation.

As shown in FIG. 14, the projections 558 are integrally formed with the base 527 and extend generally upwardly with respect to the base 527. In addition, as shown in FIG. 14, the projections 558 can extend a distance along a longitudinal direction of a biological sterilization indicator (e.g., the direction along which a container will be moved during activation), and the length and/or thickness (e.g., which can vary along the length) of the projections 558 can be tailored to control the fracturing of the container 520 at a desired position in the housing 502 and in a desired manner.

In some embodiments, the projections 558 can be adapted to fit adjacent an inner surface of a housing wall (e.g., 108 of FIGS. 1-4), such that even if the projections 558 do flex or give at all in response to a container being moved in between the projections 558, the integrity of the housing wall will provide sufficient resistance to provide the necessary force to fracture the container as desired, during activation.

In some embodiments, the projections 558 can be configured to sit a distance away from the wall 508 of the housing 502 prior to activation. In such embodiments, the projections 558 can be positioned more directly underneath the container 520 to provide more substantial support. Upon activation in such embodiments, the container 520 can be forced downward in between the projections 558, which can cause the projections 558 to flex outwardly until the projections 558 abut the wall 508 of the first portion 504 of the housing 502. At this point, the projections 558 can fracture the container 520.

As shown in FIG. 14, the upper end 559 of each of the projections 558 includes a rounded, curved or arcuate surface, which can facilitate movement of a container relative to the projections 558, and which can also inhibit premature breakage of the container and premature activation (i.e., premature release of a liquid contained in the container).

As further shown in FIG. 14, the base 527 of the insert 530 is generally U-shaped or horseshoe-shaped and includes a central aperture 577 that facilitates the movement of sterilant toward spores in a biological sterilization indicator during sterilization and also facilitates the movement of liquid contained in the frangible container (i.e., after the frangible container has been fractured) toward the spores during activation. The horseshoe shape of the base 527 includes an open side, which can create additional open space between one portion of a biological sterilization indicator and another portion of a biological sterilization indicator, as compared to a base that did not include an open side. As a result, the horseshoe shape can increase fluid communication between portions of a biological sterilization indicator.

Figure 15:
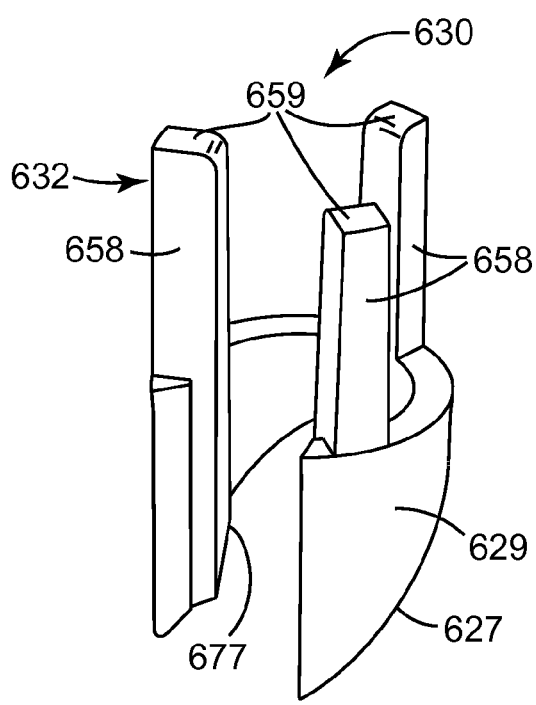
FIG. 15 is a perspective view of an insert according to another embodiment of the present disclosure.

The insert 630 illustrated in FIG. 15 is substantially the same as, and functions substantially similarly as, the insert 430 of FIGS. 10-13. The insert 630 includes three projections 658 that extend upwardly from a horseshoe-shaped base 627 that includes a central aperture 677 and that can be angled (or can include an angled surface) to fit adjacent an inner wall or partition of a biological sterilization indicator. In addition, each of the projections 658 include an at least partially rounded or arcuate upper end 659. The upper ends 659 can function as a carrier 632. The insert 630, and particularly, the carrier 632, can be adapted to hold or carry a container, such that the container is held intact in a location separate from spores during sterilization. In addition, the insert 630, and particularly, the carrier 632, can be adapted to hold the container intact a position in a biological sterilization indicator that maintains at least a minimal spacing (e.g., a minimal cross-sectional area of space) between the container and a housing or wall of the biological sterilization indicator and/or between the container and any other components or structures in the housing (e.g., at least a portion of the insert 630, such as the carrier 632, etc.), for example, to maintain a substantially constant sterilant path in the biological sterilization indicator. In some embodiments, the insert 630 can be adapted to hold the container in a substantially consistent location in the housing.

One difference between the insert 630 of FIG. 15 and the insert 430 of FIGS. 10-13 is that the insert 630 includes a sidewall 629 that extends upwardly from the base 627 and from which the projections 658 extend. Said another way, the base 627 can include a greater height (e.g., in a longitudinal direction of a biological sterilization indicator) than the base 427 of the insert 430 of FIGS. 10-13. Such a sidewall 629 can provide additional rigidity and structural integrity (e.g., to provide necessary resistance to fracture a container during activation of a biological sterilization indicator). However, the insert 430 may generally have less mass and may require less material to be manufactured.

Figure 16:
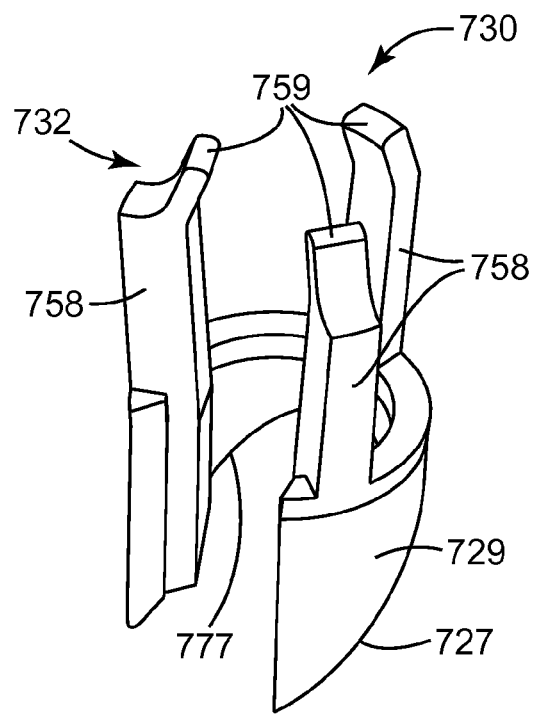
FIG. 16 is a perspective view of an insert according to another embodiment of the present disclosure.

The insert 730 illustrated in FIG. 16 is substantially the same as, and functions substantially similarly as, the insert 630 of FIG. 15. The insert 730 includes three projections 758 that extend upwardly from a horseshoe-shaped base 727 that includes a central aperture 777 and that can be angled (or can include an angled surface) to fit adjacent an inner wall or partition of a biological sterilization indicator. Similar to the insert 630 of FIG. 15, the insert 730 includes a sidewall 729 that extends upwardly from the base 727 and from which the projections 758 extend. However, one difference between the insert 730 of FIG. 16 and the insert 630 of FIG. 15 is that the projections 758 each include an upper end 759 that is angled toward the center of the insert 730. Such upper ends 759 can also be configured to be angled or directed toward a container of a biological sterilization indicator and/or a center of a biological sterilization indicator.

The upper ends 759 can be configured to support a container and hold the container above the fracturing area between the projections 758 until the container is forced downward during activation. The upper ends 759 can function as a carrier 732. The insert 730, and particularly, the carrier 732, can be adapted to hold or carry a container, such that the container is held intact in a location separate from spores during sterilization. In addition, the insert 730, and particularly, the carrier 732, can be adapted to hold the container intact a position in a biological sterilization indicator that maintains at least a minimal spacing (e.g., a minimal cross-sectional area of space) between the container and a housing or wall of the biological sterilization indicator and/or between the container and any other components or structures in the housing (e.g., at least a portion of the insert 730, such as the carrier 732, etc.), for example, to maintain a substantially constant sterilant path in the biological sterilization indicator. In some embodiments, the insert 730 can be adapted to hold the container in a substantially consistent location in the housing.

Figure 17:
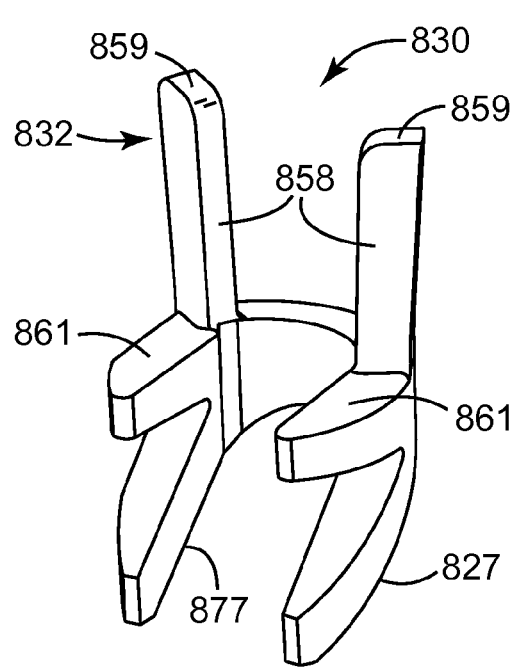
FIG. 17 is a perspective view of an insert according to another embodiment of the present disclosure.

As shown in FIG. 17, the upper ends 759 can still include a rounded surface to prevent premature breakage of a container, but the upper ends 759 also include a smaller area of contact with the container, which can both serve to prop the container up away from a region of the biological sterilization indicator where spores are located and can function to concentrate the force on a smaller area of the container as the container is forced into the interior space of the insert 730 during activation. Such concentration of force can increase the cracking/crushing pressure at these locations on the container, and can facilitate fracturing the container in a desired and reliable manner.

The insert 830 illustrated in FIG. 17 is substantially the same as, and functions substantially similarly as, the insert 530 of FIG. 14. The insert 830 includes two projections 858 that extend upwardly from a horseshoe-shaped base 827 that includes a central aperture 877 and that can be angled (or can include an angled surface) to fit adjacent an inner wall or partition of a biological sterilization indicator. In addition, each of the projections 858 include an at least partially rounded or arcuate upper end 859. The upper ends 859 can function as a carrier 832. The insert 830, and particularly, the carrier 832, can be adapted to hold or carry a container, such that the container is held intact in a location separate from spores during sterilization. In addition, the insert 830, and particularly, the carrier 832, can be adapted to hold the container intact a position in a biological sterilization indicator that maintains at least a minimal spacing (e.g., a minimal cross-sectional area of space) between the container and a housing or wall of the biological sterilization indicator and/or between the container and any other components or structures in the housing (e.g., at least a portion of the insert 830, such as the carrier 832, etc.), for example, to maintain a substantially constant sterilant path in the biological sterilization indicator. In some embodiments, the insert 830 can be adapted to hold the container in a substantially consistent location in the housing.

One difference between the insert 830 of FIG. 17 and the insert 530 of FIG. 14 is that the insert 830 includes one or more ledges 861 positioned substantially perpendicularly with respect to a longitudinal direction of a biological sterilization indicator (e.g., when the insert 830 is positioned in a biological sterilization indicator). Such ledge(s) 861 are not angled downwardly like the base 827. As a result, the ledge(s) 861 can be used for a variety of purposes. For example, the ledges 861 can stabilize the insert 830 (e.g., hold the insert 830 in a desired position in a housing of a biological sterilization indicator) under the force of fracturing a container. In addition, the ledges 861 can function to retain and/or collect fractured portions of the container after it has been fractured to inhibit movement of such portions into the proximity of spores in the biological sterilization indicator, which could negatively affect spore growth and/or detection of spore growth. Other shapes and configurations of the ledges 861 can be employed that still allow for fluid movement down to the spores (e.g., liquid after it has been released from a frangible container) while inhibiting solid movement down to the spores.

While the biological sterilization indicators 100, 200, 300 and 400 and the inserts 530, 630, 730 and 830 are described above as individual embodiments, it should be understood that a biological sterilization indicator of the present disclosure can include any combination of the various features and elements described above and shown in FIGS. 1-17 that accomplishes the desired biological sterilization indicator functions. For example, the inserts 230, 330, 430, 530, 630, 730, and 830 are illustrated and generally described as being configured to abut a wall 218, 318, 418, etc. in a biological sterilization indicator to provide force to fracture the respective container 220, 320, 420, etc. However, it should be understood that a connector, such as the connector 134 illustrated in FIGS. 1-5 and equivalents thereof, can be employed with any of the inserts 230, 330, 430, 530, 630, 730, and 830 to allow at least a portion of the insert, such as the carrier 232, 332, 432, 532, 632, 732 and 832 to move with respect to the housing of the biological sterilization indicator.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A biological sterilization indicator comprising:
   a housing including
      a first portion, and
      a second portion adapted to be coupled to the first portion, the second portion being movable with respect to the first portion between a first position and a second position;
   a container comprising a liquid, at least a portion of the container being frangible, the container positioned in at least the first portion of the housing;
   a spore reservoir positioned in the housing; and
   a projection positioned in the housing, the projection configured to
      (a) hold the container intact in a location in the housing in which a minimal cross-sectional area of space between the container and at least one of the housing and the projection is maintained when the second portion of the housing is in the first position, and
      (b) fracture the container when the second portion of the housing is moved from the first position to the second position;
   wherein the first portion of the housing includes at least one substantially planar wall positioned adjacent the spore reservoir, and wherein at least one substantially planar wall includes a detection window;
   wherein at least a portion of the projection is provided by a first portion of an insert, and wherein the insert further includes a second portion that includes the spore reservoir, wherein the insert further includes a connector configured to allow the first portion of the insert and the second portion of the insert to be moved with respect to one another.

2. The biological sterilization indicator of claim 1, wherein the projection is positioned to provide a substantially constant sterilant path in the biological sterilization indicator, the sterilant path positioned to provide fluid communication between ambience and the spore reservoir during a sterilization procedure.

3. The biological sterilization indicator of claim 1, wherein at least a portion of the insert is integrally formed with the housing.

4. The biological sterilization indicator of claim 1, wherein the first portion of the housing includes an upper portion and a lower portion, and wherein the container is positioned in the upper portion and the spore reservoir is positioned in the lower portion, and wherein the upper portion and the lower portion are separated by a wall that is oriented with respect to the longitudinal direction of the housing at a non-zero and non-right angle.

5. The biological sterilization indicator of claim 1, wherein the projection is positioned adjacent an inner surface of the first portion of the housing.

6. The biological sterilization indicator of claim 1, wherein the first portion of the housing includes a length and a tapered portion, and wherein an inner cross-sectional area of the first portion of the housing decreases in the tapered portion along at least a portion of its length.

7. The biological sterilization indicator of claim 6, wherein the spore reservoir is positioned below the tapered portion of the first portion of the housing.

8. A biological sterilization indicator comprising:
a housing including
a first portion, and
a second portion adapted to be coupled to the first portion, the second portion being movable with respect to the first portion between a first position and a second position;
a container comprising a liquid, at least a portion of the container being frangible, the container positioned in at least the first portion of the housing;
a spore reservoir positioned in the housing;
a carrier positioned to hold the container intact in a location in the housing when the second portion of the housing is in the first position, the carrier positioned to allow the container to move in response to movement of the second portion of the housing between its first position and the second position; and
a projection positioned to fracture the container when the second portion of the housing is moved from the first position to the second position;
wherein the carrier is positioned to maintain at least a minimal cross-sectional area of space defined between the container and at least one of the housing, the carrier, and the projection;
wherein the first portion of the housing includes at least one substantially planar wall positioned adjacent the spore reservoir, and wherein at least one substantially planar wall includes a detection window;
wherein the carrier is provided by an insert, wherein the insert further includes a spore reservoir, and wherein the insert further includes a connector configured to allow the carrier and the spore reservoir to be moved with respect to one another.

9. The biological sterilization indicator of claim 8, wherein the carrier is movable between a first position in which the container is not fractured and a second position in which the container is fractured.

10. The biological sterilization indicator of claim 9, wherein the first position of the carrier is a first longitudinal position in the first portion of the housing, and the second position of the carrier is a second longitudinal position in the first portion of the housing.

11. The biological sterilization indicator of claim 9, wherein the connector is positioned to allow the carrier to move between the first position and the second position.

12. The biological sterilization indicator of claim 8, wherein the connector includes a hinge.

13. The biological sterilization indicator of claim 8, wherein the carrier includes at least one arm positioned to hold the container intact when the second portion of the housing is in the first position, wherein the at least one arm is movable with respect to the container as the second portion of the housing is moved between the first position and the second position.

14. The biological sterilization indicator of claim 13, wherein the at least one arm is movable with respect to the container between a first position in which the container is not fractured and a second position in which the container is fractured.

15. The biological sterilization indicator of claim 14, wherein the first position and the second position of the at least one arm correspond to the first position and the second position of the second portion of the housing, respectively.

16. The biological sterilization indicator of claim 14, wherein the first position of the at least one arm is radially outward of the second position.

17. The biological sterilization indicator of claim 14, wherein the first portion of the housing includes a length, and a tapered portion in which an inner cross-sectional area of the first portion of the housing decreases along at least a portion of its length, and wherein the at least one arm is movable between the first position and the second position in response to the container being moved in the tapered portion of the first portion of the housing.

18. The biological sterilization indicator of claim 17, wherein the container is moved in the tapered portion of the first portion of the housing in response to the second portion of the housing being moved between the first position and the second position.

19. The biological sterilization indicator of claim 8, wherein the projection is integrally formed with the housing.

20. The biological sterilization indicator of claim 8, wherein the projection is further provided by the insert.

* * * * *

UNITED STATES PATENT AND TRADEMARK OFFICE
CERTIFICATE OF CORRECTION

PATENT NO. : 8,980,622 B2
APPLICATION NO. : 13/384886
DATED : March 17, 2015
INVENTOR(S) : Jeffrey Smith Page 1 of 1

It is certified that error appears in the above-identified patent and that said Letters Patent is hereby corrected as shown below:

In the specification

Column 4, Line 65 – delete "(1 X $10^5$ Pa)" and insert -- (1 X $10^5$ Pa). --, therefor.

Column 7, Line 49 – delete "polythyene," and insert -- polythene, --, therefor.

Column 7, Line 54 – delete "thereof" and insert -- thereof. --, therefor.

Column 9, Line 18 – delete "cellibiose," and insert -- cellobiose, --, therefor.

Column 19, Line 67 – delete "thereofIn" and insert -- thereof. In --, therefor.

Column 20, Line 14 – delete "thereof" and insert -- thereof. --, therefor.

Column 20, Line 32 – delete "thereof" and insert -- thereof. --, therefor.

Signed and Sealed this
Fifteenth Day of December, 2015

Michelle K. Lee
*Director of the United States Patent and Trademark Office*